United States Patent
Kassab et al.

(10) Patent No.: US 9,974,508 B2
(45) Date of Patent: May 22, 2018

(54) NON-INVASIVE SYSTEMS AND METHODS FOR DETERMINING FRACTIONAL FLOW RESERVE

(76) Inventors: Ghassan S. Kassab, Zionsville, IN (US); Yunlong Huo, Indianapolis, IN (US)

(*) Notice: Subject to any disclaimer, the term of this patent is extended or adjusted under 35 U.S.C. 154(b) by 429 days.

(21) Appl. No.: 13/603,073

(22) Filed: Sep. 4, 2012

(65) Prior Publication Data
US 2013/0060133 A1    Mar. 7, 2013

Related U.S. Application Data

(60) Provisional application No. 61/530,334, filed on Sep. 1, 2011.

(51) Int. Cl.
| | | |
|---|---|---|
| A61B 5/026 | (2006.01) | |
| A61B 6/00 | (2006.01) | |
| A61B 5/02 | (2006.01) | |

(52) U.S. Cl.
CPC .......... *A61B 6/504* (2013.01); *A61B 5/0263* (2013.01); *A61B 6/5217* (2013.01); *A61B 5/02007* (2013.01); *A61B 6/507* (2013.01)

(58) Field of Classification Search
None
See application file for complete search history.

(56) References Cited

U.S. PATENT DOCUMENTS

| | | | | |
|---|---|---|---|---|
| 6,471,656 | B1* | 10/2002 | Shalman et al. | 600/486 |
| 8,606,530 | B2* | 12/2013 | Taylor | 702/19 |
| 9,289,188 | B2* | 3/2016 | Bennett | A61B 8/4494 |
| 9,295,402 | B1* | 3/2016 | Arbab | A61B 5/0075 |

FOREIGN PATENT DOCUMENTS

| | | | | |
|---|---|---|---|---|
| WO | WO 03022122 A2 * | 3/2003 | | A61B 5/0215 |
| WO | WO 09094046 A1 * | 7/2009 | | A61B 5/024 |
| WO | WO 10033971 A1 * | 3/2010 | | A61B 5/1473 |

OTHER PUBLICATIONS

Pijls, N.H.J. et al., "Measurement of Fractional Flow Reserve to Assess the Functional Severity of Coronary-Artery Stenoses," N. Engl. J. Med. (1996); 334:1703-1708.*
Tonino, P.A.L. et al., "Fractional Flow Reserve versus Angiography for Guiding Percutaneous Coronary Intervention," N. Engl. J. Med. (2009); 360:213-224.*

* cited by examiner

*Primary Examiner* — Jennifer Dieterle
*Assistant Examiner* — Kevin Pontius
(74) *Attorney, Agent, or Firm* — Reichel Stohry LLP; Mark C. Reichel; Natalie J. Dean

(57) ABSTRACT

Non-invasive systems and methods for determining fractional flow reserve. At least one method of determining fractional flow reserve within a luminal organ of the present disclosure comprising the steps of positioning a monitoring device external to a luminal organ and near a stenosis, the monitoring device capable of determining at least one characteristic of the stenosis, operating the monitoring device to determine the at least one characteristic of the stenosis, and determining fractional flow reserve at or near the stenosis based upon the at least one characteristic determined by the monitoring device.

20 Claims, 15 Drawing Sheets

NON-INVASIVE SYSTEMS AND METHODS FOR DETERMINING FRACTIONAL FLOW RESERVE

RELATED APPLICATION

The present application is related to and claims the priority benefit of U.S. Provisional Patent Application Ser. No. 61/530,334, filed Sep. 2, 2011. The contents of this application are hereby incorporated by reference in their entirety into this disclosure.

BACKGROUND

Coronary heart disease remains the leading cause of morbidity and mortality in the United States and the developed world. Although the current "gold standard" for assessing coronary artery disease (CAD) is angiography, it has serious limitations in evaluating the functional significance of intermediate coronary lesions (comprising 30-70% stenosis). Coronary angiography relies on a visual interpretation of coronary anatomy. A number of studies have documented the large intra- and inter-observer variability that results from visual grading of coronary stenotic lesions. Moreover, studies have shown a lack of correlation between the angiographic delineated stenosis with their physiologic severity on coronary flow. This stems from the highly non-linear relation between the degree of stenosis and the change in blood flow. Typically, the blood flow remains unchanged until the degree of stenosis reaches a critical range (typically >80%), at which point the decrease in flow is quite dramatic. Lesions that are not functionally significant (i.e., do not reduce the flow) may not need treatment. Hence, there is a need for complementary methods to conventional coronary arteriograms that combine coronary anatomy and physiology to assess CAD accurately.

Blood vessel diameter or cross-sectional area gives anatomic measures of stenosis severity. Coronary blood flow, on the other hand, reflects coronary hemodynamic function and can be used to assess functional severity of stenosis through parameters such as coronary flow reserve (CFR) and fractional flow reserve (FFR). CFR is defined as the ratio of hyperemic (induced by pharmacological agents) to resting flow in a coronary artery. It has been previously found that a significant stenosis leading to inducible ischemia occurs when CFR has a value less than 2.0. Normally, the coronary circulation has a flow reserve of 3-5 times that of normal resting blood flow. This reserve stems from the tone of small blood vessels (microvascular bed). In disease, the microvascular bed dilates and uses some of its reserve to compensate for the pressure drop to the stenosis. Hence, a low CFR value can characterize disease in the epicardial arteries or the distal resistive microvascular bed.

Myocardial fractional flow reserve, the ratio of distal to proximal pressure of a lesion under hyperemic conditions, is an important index of coronary stenosis because it has lower variability and higher reproducibility than CFR and hyperemic stenosis resistance (HSR). The current method for the measurement of FFR requires the use of a pressure wire inserted through the stenosis (Kern, et al., Circulation 87: 1354-1367; Kern, et al., J. Am. Coll. Cardiol. 55: 173-185). Although recent advancements in sensor guidewire technology allow simultaneous measurement of distal pressure and flow velocity, there are still high variability and instability of flow velocity, occasional signal shift for pressure and guidewire obstruction of flow. The placement of pressure wire near a stenosis can also lead to overestimation of FFR. To avoid these operational shortcomings and the expense of pressure wire, a non-invasive method only based on hyperemic coronary blood flow and lesion geometry would be preferable.

In vessel segments without a stenosis, the pressure-flow curve is nearly linear in the physiological pressure range during maximal vasodilation. The linear pressure-flow relation is altered when a stenosis is present. A quadratic relation between pressure gradient ($\Delta P$) and flow rate was shown as: $\Delta P = A \cdot Q + B \cdot Q^2$, where A and B were empirical parameters determined through a curve fit of experimental data (Young, et al., J. Biomech. 6: 395-410; Young, et al., J. Biomech. 6: 547-559; Seeley, et al., J. Biomech. 6: 439-448; and Young, et al., Circ. Res. 41: 99-107). Although the quadratic relation has been experimentally validated for coronary stenosis (Siebes, et al., Circulation, 109: 756-762), the empirical parameters (A and B) are not known at priori. Hence, there is a need for a physically non-invasive physics-based model of $\Delta P$ or FFR that does not contain any empirical parameters and is specific to geometry and dynamics of coronary artery lesions. Such model would allow the prediction of functional lesion severity non-invasively to guide percutaneous coronary intervention.

BRIEF SUMMARY

In at least one embodiment of a non-invasive method for determining fractional flow reserve within a luminal organ of the present disclosure, the method comprises the steps of positioning a monitoring device external to a luminal organ at or near a stenosis, the monitoring device capable of determining at least one characteristic of the stenosis, operating the monitoring device to determine the at least one characteristic of the stenosis, and determining fractional flow reserve at or near the stenosis based upon the at least one characteristic determined by the monitoring device. The at least one characteristic, in at least one embodiment, is selected from the group consisting of a stenosis geometry and a flow rate in the luminal organ at or near the stenosis. Further, the stenosis geometry may comprise at least one geometry selected from the group consisting of a cross-sectional area of the luminal organ distal to the stenosis, a cross-sectional area of the luminal organ proximal to the stenosis, at least one cross-sectional area of the luminal organ at the stenosis, a percentage maximum stenosis of the luminal organ, and the length of the lesion of the luminal organ. Optionally, an embodiment of the non-invasive method for determining fractional flow reserve within a luminal organ may also comprise the step of diagnosing a disease based upon the determination of the fractional flow reserve within the luminal organ.

In at least one embodiment of a non-invasive method for determining fractional flow reserve within a luminal organ of the present disclosure, the determination of fractional flow reserve is indicative of a degree of stenosis within the luminal organ. Additionally, the step of determining fractional flow reserve may be performed using a data acquisition and processing system. Further, in at least one embodiment of the non-invasive method, the step of determining fractional flow comprises the step of computing the fractional flow by the data acquisition and processing system using an algorithm selected from the group consisting of a combination of Equation [4] and Equation [2]. Moreover, the monitoring device may operate to determine the at least one stenosis characteristic through angiography, such as but not limited to magnetic resonance angiography, phase shift magnetic resonance angiography, computed tomography angiography, fast computed tomography angiography, and quantitative coronary angiography.

In at least one embodiment of a non-invasive method for determining fractional flow reserve within a luminal organ of the present disclosure, the method comprises the steps of positioning a monitoring device external to a luminal organ at or near a stenosis, the monitoring device capable of determining a geometry of the stenosis and a flow rate in the luminal organ at or near the stenosis, operating the monitoring device to determine the at least one characteristic of the stenosis, and determining fractional flow reserve at or near the stenosis based upon the at least one characteristic determined by the monitoring device and by using a combination of Equation [4] and Equation [2].

In at least one embodiment of a system for non-invasively determining fractional flow reserve of a fluid within a luminal organ of the present disclosure, the system comprises a monitoring device for determining fractional flow reserve, the monitoring device operable to detect at least one stenosis characteristic of a luminal organ having a stenosis from external to the luminal organ, and a data acquisition and processing system in communication with the monitoring device, the data acquisition and processing system operable to calculate a fractional flow reserve from the at least one stenosis characteristic. The at least one stenosis characteristic may be selected from the group consisting of a stenosis geometry and a flow rate in the luminal organ at or near the stenosis. Additionally, the stenosis geometry may be comprised of at least one geometry selected from the group consisting of a cross-sectional area of the luminal organ distal to the stenosis, a cross-sectional area of the luminal organ proximal to the stenosis, at least one cross-sectional area of the luminal organ at the stenosis, a percentage maximum stenosis of the luminal organ, and the length of the lesion of the luminal organ. Further, an embodiment of the system may be capable of diagnosing a disease based upon the calculation of the fractional flow reserve within the luminal organ.

In at least one embodiment of a system for non-invasively determining fractional flow reserve of a fluid within a luminal organ of the present disclosure, the calculation of fractional flow reserve is indicative of a degree of stenosis within the luminal organ. Additionally, in at least one embodiment, the data acquisition and processing system further computes the fractional flow reserve using a combination of Equation [4] and Equation [2]. Further, in at least one embodiment the monitoring device operates to determine the at least one stenosis characteristic through angiography.

BRIEF DESCRIPTION OF THE DRAWINGS

The above mentioned embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein.

Like reference numerals indicate the same or similar parts throughout the several figures.

Figure 1:
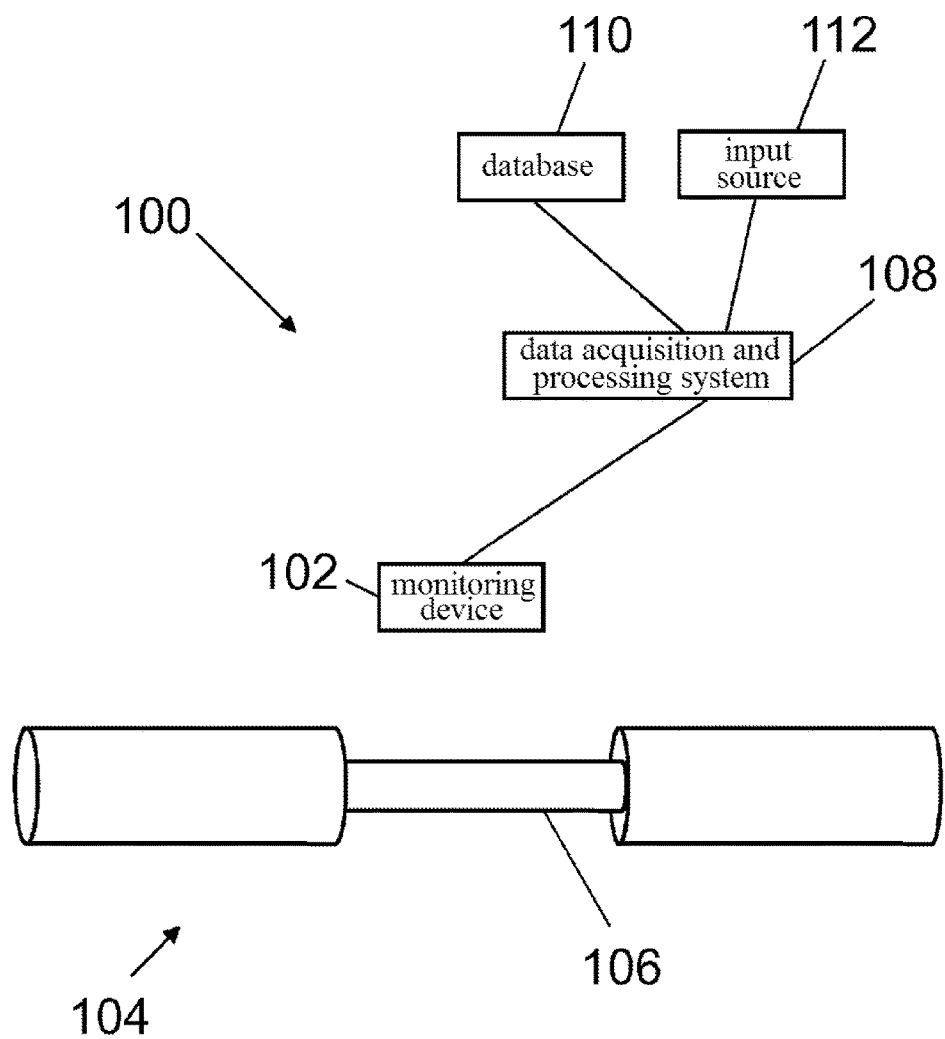
FIG. 1 shows a schematic representation of a system to determine fractional flow reserve of a luminal organ, according to an embodiment of the present disclosure.

An overview of the features, functions and/or configuration of the components depicted in the various figures will now be presented. It should be appreciated that not all of the features of the components of the figures are necessarily described. Some of these non-discussed features, such as various couplers, etc., as well as discussed features are inherent from the figures. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The disclosure of the present application provides systems and methods for determining fractional flow reserve (FFR) and/or flow rate, including exemplary systems and devices useful for performing computational determinations of FFR and/or flow rate using one or more algorithms described herein.

An exemplary embodiment of a system of the present disclosure useful to non-invasively determine FFR is shown in FIG. 1. As shown in FIG. 1, exemplary system 100 comprises a monitoring device 102 for determining FFR and/or flow rate. Monitoring device 102 is operable to detect at least one stenosis characteristic of a mammalian luminal organ 104 having a stenosis 106, while external to the mammalian luminal organ 104. Further, system 100 comprises a data acquisition and processing system 108 in communication with the monitoring device 102, wherein the data acquisition and processing system 108 is operable to calculate FFR and/or flow rate from the at least one stenosis characteristic. The mammalian luminal organ in at least one embodiment is an artery, such as the carotid artery.

An exemplary monitoring device 102 may operate through any non-invasive means available to determine the at least one stenosis characteristic of the mammalian luminal organ. For instance, the monitoring device 102 may operate using angiography on or about the stenotic region to determine the at least one stenosis characteristic. For instance, an exemplary monitoring device 102 may be operable to use at least one of magnetic resonance angiography, phase shift magnetic resonance angiography, computed tomography angiography, fast computed tomography angiography, and quantitative coronary angiography to determine the at least one stenosis characteristic of the mammalian luminal organ.

The at least one stenosis characteristic may include a stenosis geometry and/or a flow rate in the luminal organ at or near the site of stenosis. Further, the stenosis geometry may include one or more of such measurements including a cross-sectional area of the luminal organ distal to the stenosis, a cross-sectional area of the luminal organ proximal to the stenosis, at least one cross-sectional area of the luminal organ at the stenosis, a percentage maximum stenosis of the luminal organ, and the length of the lesion of the luminal organ.

Additionally, an exemplary data acquisition and processing system 108 may be in communication with a database 110 and/or an input source 112, as shown in FIG. 1. The database 110 may contain one or more variable about the mammal containing the stenosis (such as identifying characteristics, medically relevant information, and/or one or more stenosis characteristic). Further, the input source 112 may be operable to introduce at least one instruction required to determine the FFR, the flow rate, or at least one stenosis characteristic useful to determine the FFR and/or flow rate.

An exemplary data acquisition and processing system 108 may use one or more equation to compute the FFR and/or flow rate at or about the stenosis. Exemplary equations used to compute the FFR include at least a combination of Equation [4] and Equation [2], as referenced in more detail herein. Further, an exemplary data acquisition and processing system 108 may use one or more equation, such as Equation [A1], to compute the flow rate at or about the stenosis. Specifically, in an exemplary embodiment of data acquisition and processing system 108, system 108 may be configured to use the cross sectional area at or about the stenosis to calculate the flow rate at or about the stenosis using one or more equations of the present disclosure.

Additionally, an exemplary data acquisition and processing system 108 may use equations of one or both of the methods of the pulsatile method to determine FFR or the steady-state method to determine FFR as described in greater detail herein. In an exemplary embodiment, such equations may include at least one of equations [1.1], [2.1], [2.2], [2.7], [2.8], [3.1], [3.2], [3.3], and [3.4].

Moreover, an exemplary data acquisition and processing system 108 may also be able to compare the calculated FFR to a comparison value in database 110 to determine the degree of stenosis, or another relevant disease or condition.

Figure 2A:
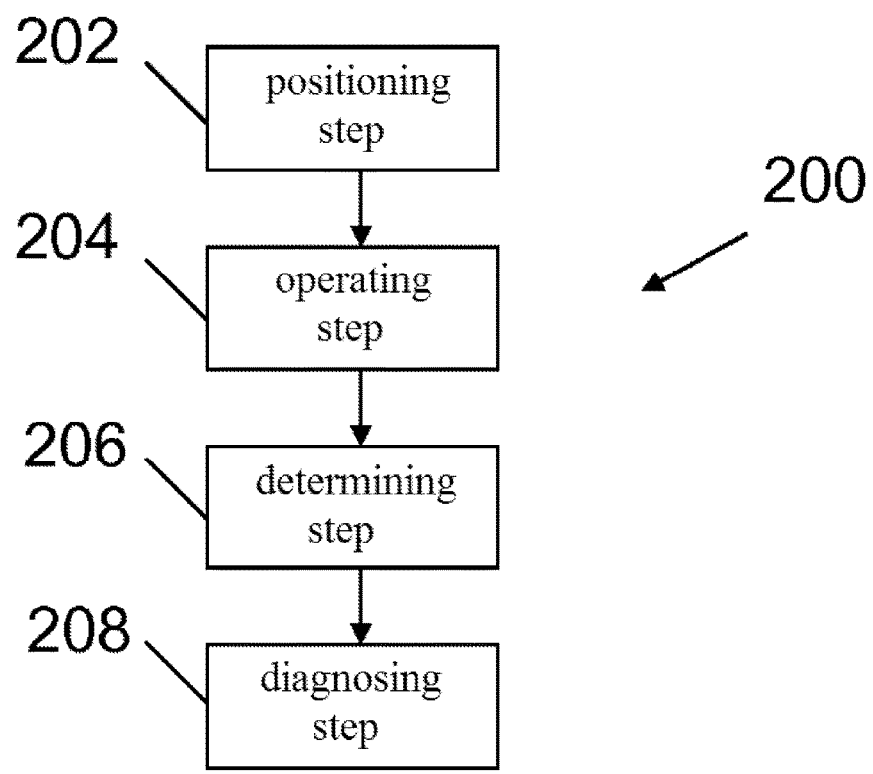
FIG. 2 shows a flowchart depicting the steps of a method to determine the fractional flow reserve of a luminal organ, according to an embodiment of the present disclosure.

An exemplary embodiment of a method of non-invasively determining FFR of the present disclosure is depicted in FIG. 2A. Exemplary method 200 comprises the steps of positioning a monitoring device external to a luminal organ and near a stenosis, where the monitoring device is capable of determining at least one characteristic of the stenosis (an exemplary positioning step 202), operating the device to determine the at least one characteristic of the stenosis (an exemplary operating step 204), and determining fractional flow reserve at or near the stenosis based upon the at least one characteristic determined by the monitoring device (an exemplary determining step 206). Additionally, exemplary method 200 may also comprise a step of diagnosing a disease based upon the determination of the FFR within the luminal organ (an exemplary diagnosing step 208).

Figure 2B:
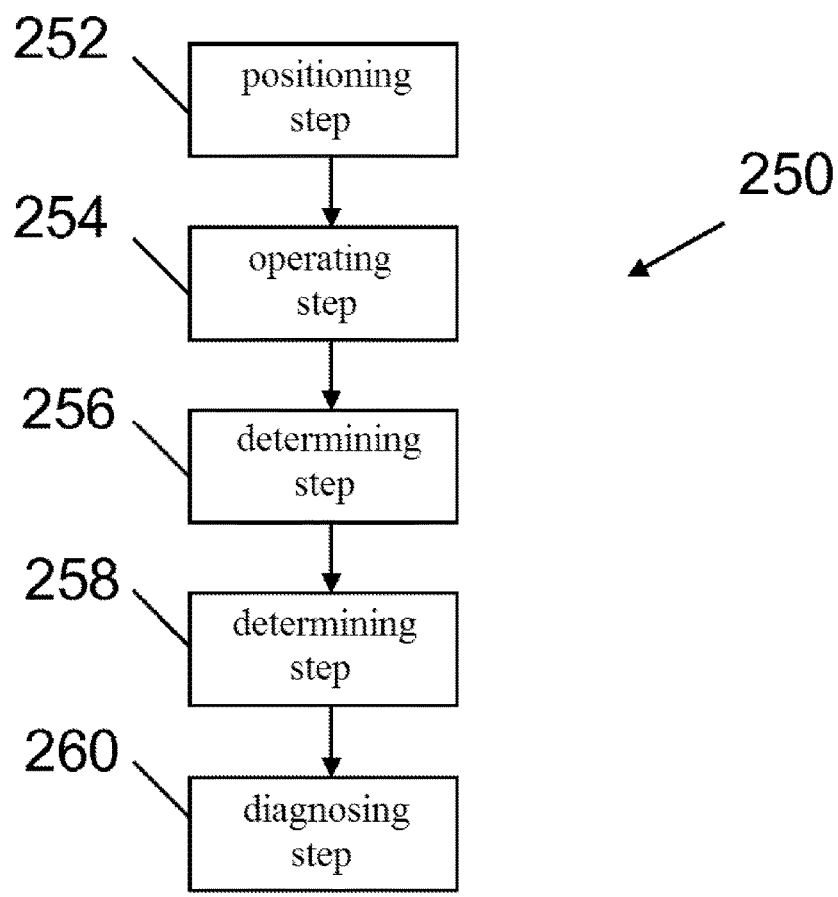

Turning to FIG. 2B, an exemplary embodiment of a method of non-invasively determining the flow rate in a luminal organ of the present disclosure is shown. Exemplary method 250 comprises the steps of positioning a monitoring device external to a luminal organ and near a stenosis, where the monitoring device is capable of determining at least one characteristic of the stenosis (an exemplary positioning step 252), operating the device to determine the at least one characteristic of the stenosis (an exemplary operating step 254), and determining flow rate at or near the stenosis based upon the at least one characteristic determined by the monitoring device and using at least one equation described herein (an exemplary determining step 256). Additionally, exemplary method 250 may also comprise the step of determining the fractional flow reserve at or near the stenosis based upon the at least one characteristic determined by the monitoring device and the flow rate determined in step 256 (an exemplary determining step 258). Further, exemplary method 200 may also comprise a step of diagnosing a disease based upon the determination of the FFR within the luminal organ (an exemplary diagnosing step 260).

An exemplary operating step 204 or 254 of the present disclosure may include the determination of at least one of a cross-sectional area of the luminal organ distal to the stenosis, a cross-sectional area of the luminal organ proximal to the stenosis, at least one cross-sectional area of the luminal organ at the stenosis, a percentage maximum stenosis of the luminal organ, and the length of the lesion of the luminal organ. Such variables determined in step 254 may be used to determine the flow rate at the stenosis through using the determined variables with an equation described herein (such as Equation [2]). Accordingly, in at least one embodiment of step 254, at least one cross-sectional area of the luminal orgain at the stenosis can be used with Equation [A1] to determine the flow rate.

An exemplary determining step 206 or 256 of the present disclosure may include the step of computing the FFR through the use of a combination of Equation [4] and Equation [2] (both of which are described in further detail below). Additionally, an exemplary operating step 204 may involve the performance of angiogenesis on or around the region of stenosis. Further, and as generally referenced herein, emplary positioning step 202 and operating step 204 are non-invasive to the patient.

Additionally, an exemplary determining step 206 or 256 of the present disclosure may include the step of computing the FFR through the use of at least one of Equations [1.1], [2.1], [2.2], [2.7], [2.8], [3.1], [3.2], [3.3], and [3.4].

Myocardial FFR

Myocardial FFR is a functional parameter of stenosis severity. FFR during hyperemic flow is given by:

$$FFR = \frac{P_{distal} - P_v}{P_a - P_v} \quad [1]$$

where $P_a$ is the mean aortic pressure ($P_a \approx P_{proximal}$ assuming no diffuse coronary artery disease), and $P_v$ is the central venous pressure, and $P_{proximal}$ and $P_{distal}$ are the hyperemic coronary pressure proximal and distal to stenosis, respectively (Pijls, et al., Circulation 87: 1354-1367). If the central venous pressure is assumed to be negligible, Equation [1] is generally simplified to:

$$FFR = \frac{P_{distal}}{P_a} = \frac{P_a - \Delta P}{P_a} \quad [2]$$

where $\Delta P$ is the pressure gradient along the axis of luminal organ segment from proximal to distal position of stenosis.

Pressure Gradient Across Stenosis

The present disclosure includes disclosure of a novel model to determine $\Delta P$ for mammalian luminal organs, such as coronary arteries. Since gravity is negligible in the coronary circulation, the general Bernoulli equation can be written as $$\Delta P = \frac{\rho Q^2}{2}\left(\frac{1}{CSA_{outlet}^2} - \frac{1}{CSA_{inlet}^2}\right) + \sum \text{energy loss} \quad [3]$$

where $$\frac{\rho Q^2}{2}\left(\frac{1}{CSA_{outlet}^2} - \frac{1}{CSA_{inlet}^2}\right)$$

is the convective energy loss, $CSA_{inlet}$ and $CSA_{outlet}$ are the inlet and outlet cross-sectional areas, respectively, Q is the hyperemic flow rate in a vessel segment, and $\rho$ is the density of blood.

There are three other major energy losses: diffusive energy loss ($\Delta P_{diffusive}$), energy loss due to sudden constriction in CSA from proximal normal vessel segment to stenosis ($\Delta P_{constriction}$), and energy loss due to sudden enlargement in CSA from stenosis to distal normal vessel segment ($\Delta P_{expansion}$) expansion). Although $\Delta P_{diffusive}$ is generally caused by the viscosity in the fully-developed region (i.e., viscous energy loss in this case), the pressure drop serves both to accelerate the flow and to overcome viscous drag in the entrance region of a stenosis, which contribute to the diffusive energy loss (see FIG. 3C). Moreover, the energy loss due to sudden constriction is relatively small (loss coefficient<<0.1 generally) if the flow transition, from proximal normal vessel to stenosis, is well-bound and follows the streamlines. Further, the energy loss due to sudden constriction is negligible. Equation [3] can thus be rewritten as:

$$\Delta P = \frac{\rho Q^2}{2}\left(\frac{1}{CSA_{outlet}^2} - \frac{1}{CSA_{inlet}^2}\right) + \Delta P_{diffusive} + \Delta P_{expansion} \quad [4]$$

In at least one embodiment of the method or system of the present disclosure, Equation [4] may be combined with Equation [2] to determine FFR from the stenosis geometry and hyperemic flow, as provided in further detail herein.

Figure 3A:
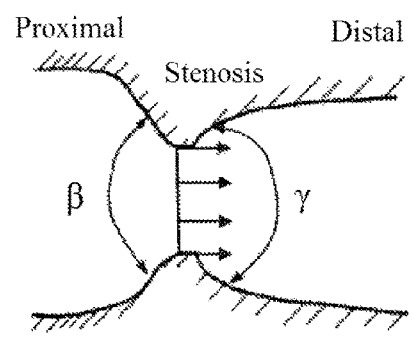
FIGS. 3A-C show schematic representations of (A) a thin stenosis, (B) a short stenosis, and (C) a long stenosis, according to embodiments of the present disclosure.
Figure 3B:
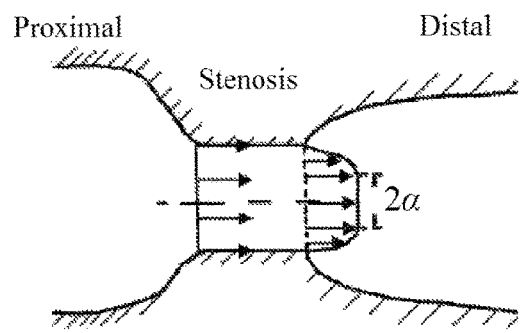
Figure 3C:
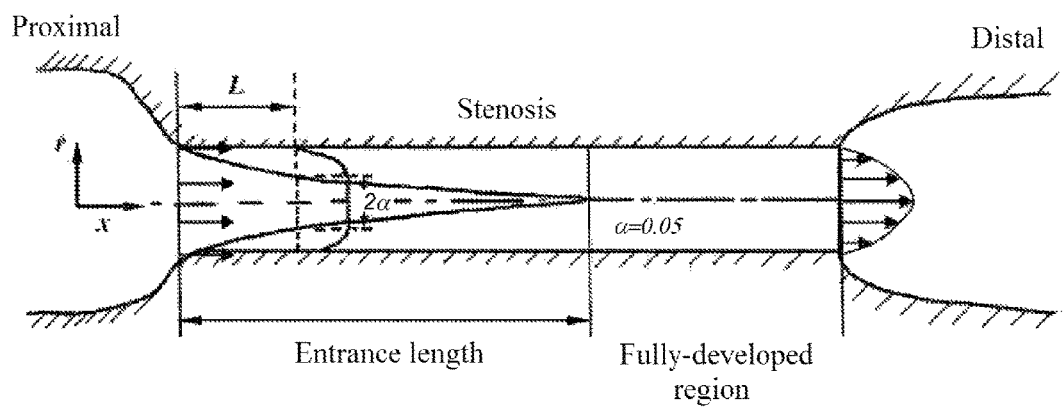

The blood flow in coronary arteries is largely laminar because of the low Reynolds number. Based on the luminal organ length, a single stenosis can be divided into three types: 1) a thin orifice (FIG. 3A shows the stenosis length close to zero); 2) a short stenosis (FIG. 3B shows the entire stenosis in the entrance region); and 3) a long stenosis (FIG. 3C shows the stenosis comprised of the entrance and fully-developed regions). The diffusive energy loss is generally caused by the viscosity in the fully-developed region, as shown in FIG. 3C. However, the pressure drop serves both to accelerate the flow and to overcome viscous drag in the entrance region, which is attributed to the diffusive energy loss in the present study.

The Poiseuille formula is generally applied to blood flow in a fully-developed region, which is written as:

$$-dp = \frac{8\pi\mu}{CSA^2} Q dx \quad [A1]$$

where p is the pressure, $\mu$ is the dynamic viscosity, and Q is the flow rate in the luminal organ. For the entrance region, a dimensionless radius of inviscid core ($\alpha$) is defined, in which the flow velocity is uniform such as $\alpha = r$ at the inlet, $0 < \alpha < r$ from the inlet to the fully-developed region, $\alpha = 0$ at the fully-developed region, as shown in FIGS. 3A-C, respectively. A non-dimensional entrance length from the inlet (x=0) to a position (x=L), as shown in FIG. 3C, can be written as:

$$\frac{L}{Re \cdot D} = \frac{\pi \mu L}{4\rho Q} \quad [A2]$$

$$= \frac{1}{4}\int_\alpha^1 \frac{(1-\alpha)(6+\alpha)(1+4\alpha+9\alpha^2+4\alpha^3)}{5\alpha(3+2\alpha)(3+2\alpha+\alpha^2)^2} d\alpha$$

where L is the axial distance, D is the inlet diameter, and $$Re = \frac{4\rho Q}{\pi D \mu}$$

is the Reynolds number. Here, $\alpha = 0.05$ refers to the end of entrance region (i.e., the beginning of fully-developed region), as shown in FIG. 3C. Accordingly, the dimensionless pressure drop $$\left(\frac{\Delta P}{\frac{\rho \cdot Q^2}{2 \cdot CSA^2}}\right)$$

in the entrance length (L) is written as:

$$\frac{\Delta P}{\frac{\rho \cdot Q^2}{2 \cdot CSA^2}} = \frac{96}{5}\int_\alpha^1 \frac{(1+4\alpha+9\alpha^2+4\alpha^3)}{\alpha(3+2\alpha)(3+2\alpha+\alpha^2)^2} d\alpha \quad [A3]$$

where αP is the pressure drop in the entrance length (L). Since the stenosis entrance dominates the pressure drop over the normal luminal organ entrance, the effect of normal luminal organ entrance can be negligible due to the relatively large CSA.

When there is a uniform flow velocity at the luminal organ proximal to the stenosis, the energy loss due to an abrupt constriction in CSAs can be written as:

$$\Delta P_{constriction} = \frac{\rho Q^2}{2} \cdot \frac{1}{2} \cdot \left( \frac{1}{CSA_{stenosis}^{8/3}} - \frac{1}{CSA_{proximal} \cdot CSA_{stenosis}^{5/3}} \right)^{\frac{3}{4}} \quad [A4]$$

If the flow velocity profile is parabolic (which is determined by the length of the normal luminal organ proximal to the stenosis), the energy loss can be written as:

$$\Delta P_{constriction} = \frac{\rho Q^2}{2} \cdot \frac{6}{\pi} \cdot \frac{\left( \frac{1}{R_{stenosis}^4} - \frac{1}{R_{stenosis}^2 \cdot R_{proximal}^2} \right)}{Re_{stenosis}} \quad [A5]$$

where αP$_{constriction}$ is the pressure drop due to an abrupt constriction in CSAs; CSA$_{stenosis}$ and CSA$_{proximal}$ are the cross-sectional areas and R$_{stenosis}$ and R$_{proximal}$ are the radiuses at the stenosis and just proximal to the stenosis, respectively;

$$Re_{stenosis} = \frac{2\rho Q}{\pi \mu R_{stenosis}}$$

is the Reynolds number at the inlet of stenosis. Since the pressure loss of a constriction can be significantly reduced (loss coefficient<<0.1 generally) with a luminal organ boundary following the flow streamlines (i.e., there is no plane of vena contracta for the incompressible, laminar coronary blood flow), the energy loss due to sudden constriction is assumed to be negligible in the present study except for angle β (in FIG. 3A) when greater than 150°.

Unlike sudden constriction, there is a large energy loss for sudden enlargement that must be included. If angle γ (in FIG. 3A) is less than 45°, we neglect the energy loss because the coronary artery can be clinically presumed to be normal in the absence of diffuse disease. When there is a uniform flow velocity at the outlet of stenosis, the energy loss due to an abrupt expansion in CSA can be determined from the one-dimensional continuity, momentum and energy equations, which can be written as:

$$\Delta P_{expansion}^{uniform} = \frac{\rho Q^2}{2} \left( \frac{1}{CSA_{stenosis}} - \frac{1}{CSA_{distal}} \right)^2 \quad [A6]$$

If the flow velocity profile is parabolic at the outlet of stenosis, the energy loss can be written as:

$$\Delta P_{expansion}^{parabolic} = \quad [A7]$$
$$\rho Q^2 \cdot \left( \frac{1}{CSA_{stenosis}} - \frac{1}{CSA_{distal}} \right) \cdot \left( \frac{1}{CSA_{stenosis}} - \frac{1}{3} \cdot \frac{1}{CSA_{distal}} \right)$$

where ΔP$_{expansion}$ is the pressure drop due to an abrupt expansion in CSA; CSA$_{stenosis}$ and CSA$_{distal}$ are the cross-sectional areas at the stenosis and just distal to the stenosis, respectively; Moreover, if the velocity profile is blunt at the outlet of stenosis (see FIG. 3B), the pressure drop may be determined using the interpolation as:

$$\Delta P_{expansion}^{blunt} = \Delta P_{expansion}^{uniform} + (\Delta P_{expansion}^{parabolic} - \Delta P_{expansion}^{uniform}) \cdot (1-\alpha)^2 \quad [A8]$$

where α is the dimensionless radius of inviscid core.

Since the energy loss due to sudden constriction in CSA has been omitted herein, the total pressure drop across a stenosis, ΔP$_{stenosis}$, can be written as:

$$\Delta P_{stenosis} = \quad [A9]$$
$$\frac{\rho Q^2}{2 \cdot CSA_{stenosis}^2} \frac{96}{5} \int_\alpha^1 \frac{(1+4\alpha+9\alpha^2+4\alpha^3)}{\alpha(3+2\alpha)(3+2\alpha+\alpha^2)^2} d\alpha + \Delta P_{expansion}^{blunt}$$

if $\alpha \geq 0.05$ for $\frac{L_{stenosis}}{Re_{stenosis} \cdot D_{stenosis}}$ $$\Delta P_{stenosis} = \frac{\rho Q^2}{2 \cdot CSA_{stenosis}^2} \frac{96}{5} \int_{0.05}^1 \frac{(1+4\alpha+9\alpha^2+4\alpha^3)}{\alpha(3+2\alpha)(3+2\alpha+\alpha^2)^2} d\alpha + \quad [A10]$$
$$\int_0^{L_{stenosis}-L_{entrance}} \frac{8\pi\mu}{CSA_{stenosis}^2} Q dx + \Delta P_{expansion}^{parabolic}$$

if $\alpha < 0.05$ for $\frac{L_{stenosis}}{Re_{stenosis} \cdot D_{stenosis}}$ where L$_{stenosis}$ is the length of stenosis, L$_{entrance}$ is the entrance length with α=0.05, and the length of stenosis minus the entrance length (L$_{stenosis}$−L$_{entrance}$) equals to the length of fully-developed segment.

If the entire length of the stenosis in a luminal organ is in the entrance region (α≥0.05 corresponding to Equation A9), the total pressure drop across the luminal organ can be written as:

$$\Delta P = \frac{\rho Q^2}{2} \cdot \left( \frac{1}{CSA_{outlet}^2} - \frac{1}{CSA_{inlet}^2} \right) + \quad [A11]$$
$$\frac{\rho Q^2}{2 \cdot CSA_{stenosis}^2} \frac{96}{5} \int_\alpha^1 \frac{(1+4\alpha+9\alpha^2+4\alpha^3)}{\alpha(3+2\alpha)(3+2\alpha+\alpha^2)^2} d\alpha +$$
$$\int_0^{L_{vessel}-L_{stenosis}} \frac{8\pi\mu}{CSA^2} Q dx + \frac{\rho Q^2}{2} \cdot$$
$$\left\{ \left( \frac{1}{CSA_{stenosis}} - \frac{1}{CSA_{distal}} \right)^2 + \left[ 2 \cdot \left( \frac{1}{CSA_{stenosis}} - \frac{1}{CSA_{distal}} \right) \cdot \left( \frac{1}{CSA_{stenosis}} - \frac{1}{3} \cdot \frac{1}{CSA_{distal}} \right) - \left( \frac{1}{CSA_{stenosis}} - \frac{1}{CSA_{distal}} \right)^2 \right] \cdot (1-\alpha)^2 \right\}$$

If the entire length of the stenosis in a luminal organ includes the entrance and fully-developed segments (α<0.05 corresponding to Equation [A10]), the total pressure drop across the luminal organ can be written as:

$$\Delta P = \frac{\rho Q^2}{2} \cdot \left( \frac{1}{CSA_{outlet}^2} - \frac{1}{CSA_{inlet}^2} \right) + \quad [A12]$$
$$\frac{\rho Q^2}{2 \cdot CSA_{stenosis}^2} \frac{96}{5} \int_{0.05}^1 \frac{(1+4\alpha+9\alpha^2+4\alpha^3)}{\alpha(3+2\alpha)(3+2\alpha+\alpha^2)^2} d\alpha +$$

-continued $$\int_0^{L_{vessel}-L_{entrance}} \frac{8\pi\mu}{CSA^2} Qdx +$$

$$\rho Q^2 \cdot \left(\frac{1}{CSA_{stenosis}} - \frac{1}{CSA_{distal}}\right) \cdot \left(\frac{1}{CSA_{stenosis}} - \frac{1}{3} \cdot \frac{1}{CSA_{distal}}\right)$$

Equations [A11] and [A12] were used to determine the total pressure drop across a luminal organ with a single stenosis.

Figure 4:
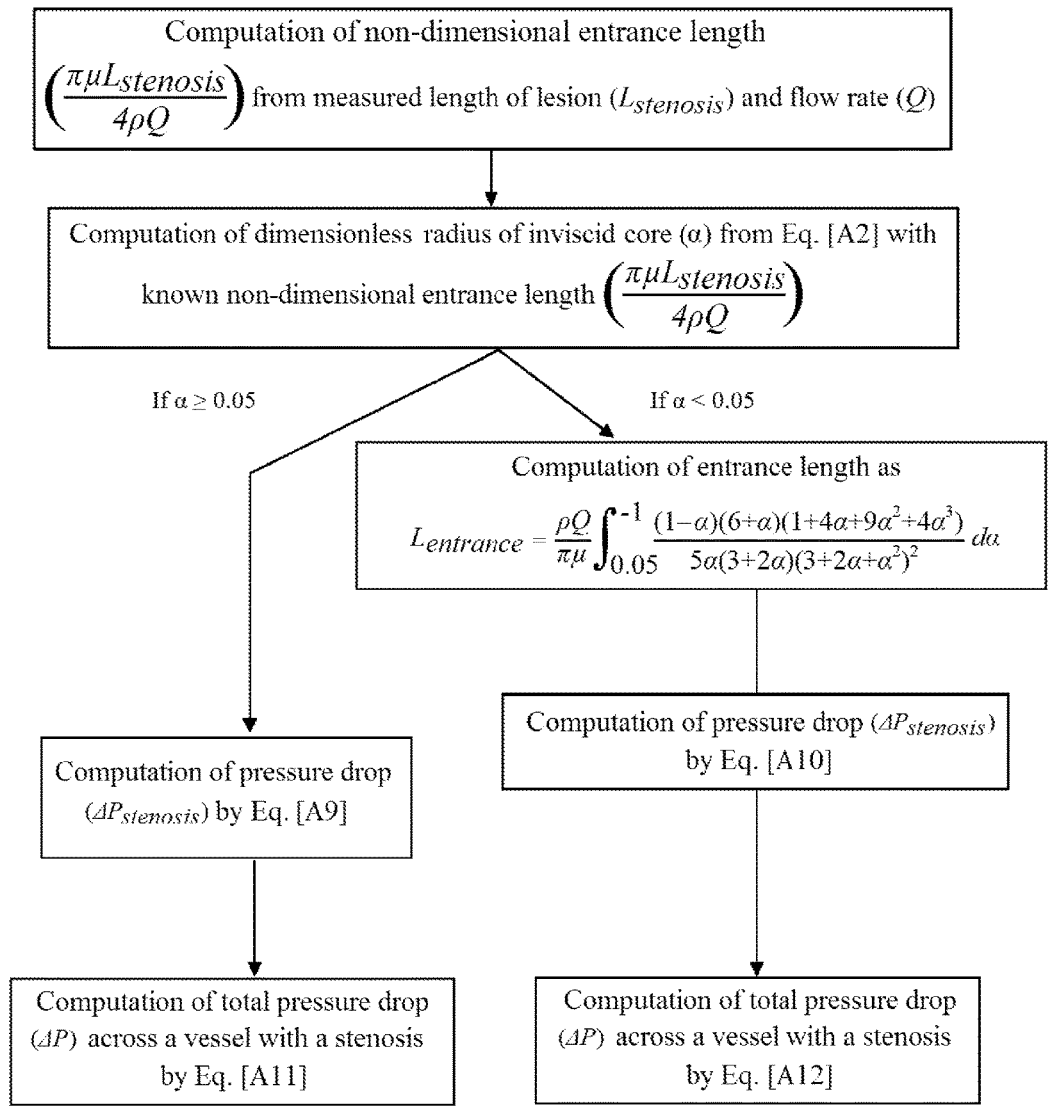
FIG. 4 shows a flow diagram showing steps to determine the total energy loss across a luminal organ with a stenosis, according to an embodiment of the present disclosure.

FIG. 4 shows a flow diagram for determination of energy loss across a luminal organ in the presence of a single stenosis. Briefly, the length of stenosis ($L_{stenosis}$) and flow rate (Q) are initially used to calculate the non-dimensional entrance length $$\left(\frac{L_{stenosis}}{Re_{stenosis} \cdot D_{stenosis}} \text{ or } \frac{\pi\mu L_{stenosis}}{4\rho Q}\right).$$

The dimensionless radius of inviscid core ($\alpha$) is then calculated from Equation [A2] with the known non-dimensional entrance $$\left(\frac{\pi\mu L_{stenosis}}{4\rho Q}\right).$$

If $\alpha \geq 0.05$, the entire stenosis is assumed to be in the entrance region and the pressure drops across the stenosis and luminal organ can be determined by Equations [A9] and [A11], respectively. If $\alpha < 0.05$, the entire stenosis can be divided into the entrance and fully-developed segments, where the entrance length $L_{entrance}$ is obtained from Equation [A2] with $\alpha = 0.05$ and the pressure drops across the stenosis and luminal organ can be determined by Equations [A10] and [A12], respectively.

Flow Determination Across the Stenosis

The flow-diameter scaling law can be written as:

$$Q_s = K_Q D_s^{\frac{7}{3}},$$

where $Q_s$ (ml) and $D_s$ (cm) are the flow and diameter and $K_Q$ equals to 10 in arterial trees (see exemplary tree in FIG. 5) at aortic pressure of 100 mmHg. There is a pressure gradient of about 1 mmHg between aortic pressure and coronary arteries visible with conventional imaging (~1 mm). Therefore, the resistance (dynes·cm·s$^{-1}$; 1333.22 is the unit conversion from mmHg) at coronary arteries with diameter of ~1 mm can be calculated as:

$$\text{Resistance} = \frac{99 \times 1333.22}{10 \times D_s^{7/3}} = \frac{13199}{10 \times D_s^{7/3}} \quad [1.1]$$

The resistance determined from equation [1.1] may be applied to each outlet of the epicardial coronary arterial tree obtained from CT scans, biplane-angiography, 3D IVUS or other non-invasive imaging.

Pulsatile Method for FFR Determination

Once the aortic pressure is known, the blood flow in the epicardial coronary arterial tree can be calculated using a frequency model (where $\omega \to 0$ denotes steady state) (Huo Y, Kassab G S. Pulsatile blood flow in the entire coronary arterial tree: theory and experiment. Am J Physiol Heart Circ Physiol. 2006; 291(3):H1074-1087). Briefly, in a frequency domain, the governing equations for flow (Q) and pressure (P) (transformed from the conversion of mass and momentum) in a vessel are written as:

$$Q(x,\omega) = a \cos(\omega x/c) + b \sin(\omega x/c) \quad [2.1]$$

$$P(x,\omega) = iZ_1[-a \sin(\omega x/c) + b \cos(\omega x/c)] \quad [2.2]$$

where a and b are arbitrary constants of integration, $\omega$ the angular frequency, $$c = \sqrt{1-F_{10}(\alpha)} \cdot c_0 \left(c_0 = \sqrt{\frac{Eh}{\rho R}}\right)$$

is the wave velocity, h/R the ratio of wall thickness to radius, E the Young's modulus, $\rho$ the density, and $$F_{10}(\alpha) = \frac{2J_1(i^{3/2}\alpha)}{i^{3/2}\alpha J_0(i^{3/2}\alpha)} \quad \left(\alpha = \frac{D}{2}\sqrt{\frac{\omega\rho}{\mu}}\right),$$

$\mu$ is the dynamic viscosity, $J_0$ the Bessel function of zero order and first kind, and $J_1$ the Bessel function of first order and first kind).

$$Y_0 = \frac{A(n)}{\rho c_0}$$

is defined as the characteristic admittance, $Z_0 = 1/Y_0$ the characteristic impedance, $Y_1 = Y_0\sqrt{1-F_{10}(\alpha)}$, and $Z_1 = Z_0/\sqrt{1-F_{10}(\alpha)}$. The impedance and admittance in a vessel is:

$$Z(x,\omega) = \frac{P(x,\omega)}{Q(x,\omega)} = \frac{iZ_1[-a\sin(\omega x/c) + b\cos(\omega x/c)]}{a\cos(\omega x/c) + b\sin(\omega x/c)} \quad [2.3]$$

$$Y(x,\omega) = \frac{1}{Z(x,\omega)} \quad [2.4]$$

In a given vessel segment, at x=0 and x=L, the inlet and outlet impedance are:

$$Z(0,\omega) = \frac{iZ_1 b}{a} \quad [2.5]$$

$$Z(L,\omega) = \frac{iZ_1[-a\sin(\omega L/c) + b\cos(\omega L/c)]}{a\cos(\omega L/c) + b\sin(\omega L/c)} \quad [2.6]$$

A combination of Eqs. [2.5] and [2,6] yields:

$$Z(0,\omega) = \frac{iZ_1\sin(\omega L/c) + Z(L,\omega)\cos(\omega L/c)}{\cos(\omega L/c) + iY_1 Z(L,\omega)\sin(\omega L/c)} \quad [2.7]$$

Since there are two or more vessels that emanate from the jth junction point of the entire RCA tree, the junction boundary condition (determined from the continuous pressure and mass conservation) is written as:

$$Y[L(\text{mother}),\omega] = \Sigma Y[0(\text{daughters}),\omega] \quad [2.8]$$

Figure 5:
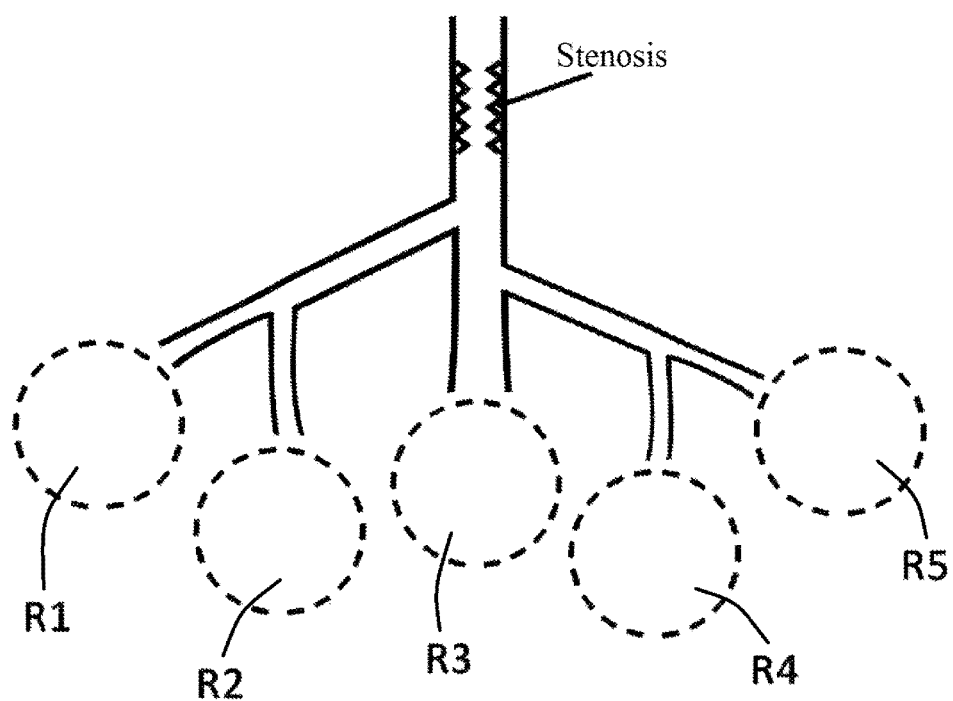
FIG. 5 shows a schematic representation of a vessel tree, where the vessel contains a stenosis, according to an embodiment of the present disclosure.
Figure 6:
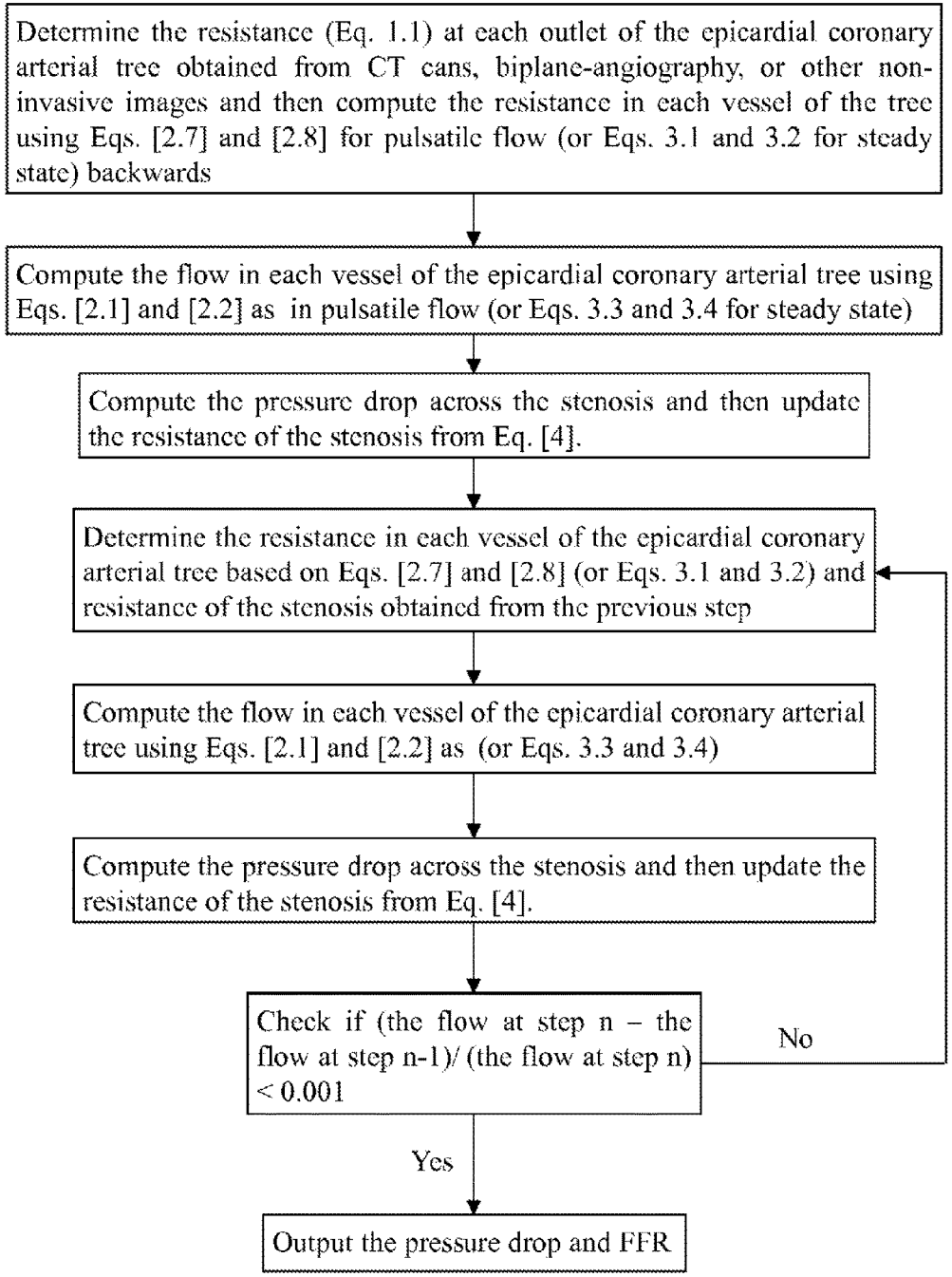
FIG. 6 shows a flow diagram showing steps to determine the FFR of a luminal organ with a stenosis, according to an embodiment of the present disclosure.

Based on the resistance in equation [1.1], calculations can proceed backwards (from daughter to mother vessels, as shown in FIG. 5) to determine the impedance (or admittance) in each vessel of the epicardial arterial tree using Eq. [2.7] and Eq. [2.8]. In at least one embodiment, FIG. 5 shows a schematic representation of the epicardial coronary arterial tree, where R1-R5 refer to the outlets of the epicardial arterial tree. The flow and pressure as $\omega \rightarrow 0$ are then calculated by using Eqs. [2.1-2.2]. Moreover, the flow through the stenotic vessel can be used to determine the pressure drop and resistance across the stenosis from the stenotic Equation [4]. The updated resistance of stenosis will be used in the epicardial coronary arterial tree for determination of the blood flow iteratively until the preset criteria is satisfied (see the flow chart in FIG. 6). Finally, the FFR can be determined by Equation [2].

Steady-State Method for FFR

At least one alternative exemplary method to determine FFR based on a steady state analysis is shown. In a given blood vessel, the steady-state resistance for a vessel is:

$$Z(0) = \frac{8\mu L}{\pi R^4} + Z(L) \quad [3.1]$$

The junction boundary condition (determined from the continuous pressure and mass conservation) is:

$$\frac{1}{Z[L(\text{mother})]} = \sum \frac{1}{Z[0(\text{daughters})]} \quad [3.2]$$

The steady-state pressure change in a vessel is:

$$P(L) = P(0) - \frac{8\mu L}{\pi R^4} \frac{P(0)}{Z(0)} \quad [3.3]$$

Further, at the junction, the pressure in mother vessel equals to that in daughter vessels as:

$$P[L(\text{mother})] = P[0(\text{daughter})] \quad [3.4]$$

Similar to the pulsatile method outlined above, based on the resistance in equation [1,1], calculations can proceed backwards (from daughter to mother vessels, as shown in FIG. 1) to determine the impedance (or admittance) in each vessel of the epicardial arterial tree using Eq. [3.1] and Eq. [3.2]. The steady-state flow and pressure are then calculated by using Eqs. [3.3-3.4]. Moreover, the flow through the stenotic vessel can be used to determine the pressure drop and resistance across the stenosis from Equation [4]. The updated resistance of stenosis will be used in the epicardial coronary arterial tree for determination of the blood flow iteratively until the preset criteria is satisfied (see flow chart in FIG. 6). Finally, the FFR can be determined by the respective Equation [4].

While various embodiments of systems for determining fractional flow reserve and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

EXAMPLES

1. In Vivo and In Vitro Validation

In vitro and in vivo experiments were used to validate the analytical model of pressure drop (Equation [4]) and FFR (Equation [2]). Studies were performed on eight domestic swine weighing 60-70 kg. The geometrical parameters and flow rates in blood vessel and stenosis for in vitro and in vivo experiments are listed in Table 1.

Surgical anesthesia for the experimental subjects was induced with TKX (Telazol 500 mg, Ketamine 250 mg, Xylazine 250 mg) and maintained with 2% isoflurane. The animals were intubated and ventilated with room air and oxygen by a respiratory pump. A side branch from the left jugular vein was dissected and cannulated with a 7 Fr. sheath for administration of drugs (e.g., heparin, lidocaine, levophed, and saline as needed). The right femoral artery was cannulated with a 7 Fr sheath and then a guide catheter was inserted to measure the aortic blood pressure using a transducer (Summit Disposable Pressure Transducer, Baxter Healthcare; error of ±2% at full scale).

Figure 7A:
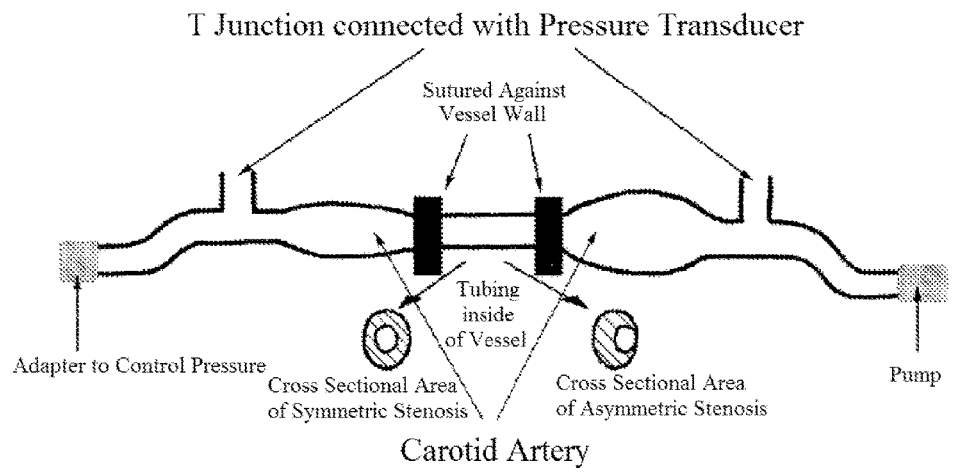
FIGS. 7A-B show a schematic representation of an in vitro stenosis set-up with (A) insertion of known sizes of concentric and eccentric tubing into the carotid artery to mimic various stenoses and (B) an inflatable arterial occluder to create various stenoses, according to embodiments of the present disclosure.

For the in vitro experiments, carotid arteries were dissected and isolated and small branches were ligated by suture. Further, and as shown in FIGS. 7A and B, the segments of the carotid artery used were connected to a pump at one end and an adapter at the other end to control pressure. Several tubings (concentric and eccentric) and an inflatable occluder cuff (OC4, In Vivo Metric) were used to create various stenoses (FIGS. 7A, B), Table 1 shows the geometry and flow rate in carotid arteries and tubings. In one in vitro set-up, various sizes of concentric and eccentric tubings were inserted into carotid artery and ligated against the vessel wall to form symmetric and asymmetric stenoses, as shown in FIG. 7A. Such tubings were structured so that the stenosis generated had diameters ranging from 0.85 mm to 2.1. Specifically the stenotic diameters in various examples were 0.85 mm, 1.2 mm, 1.7 mm or 2.1 mm for the symmetric tubing, and 0.85 mm or 1.3 mm for the asymmetric tubing. Further, for stenosis generated by occluder cuffs, the stenosis diameters ranged 1.25 mm to 2 mm for in vitro set-ups to 1.1 mm to 2 mm for in vitro set-ups. The stenosis eccentricity ranged from zero to 0.8 (defined as $$\frac{D_{axis}}{R_{proximal}},$$

where $D_{axis}$ is the distance of centerlines between stenosis and proximal vessel segment and $R_{proximal}$ is the radius of the proximal vessel segment to stenosis).

Figure 7B:
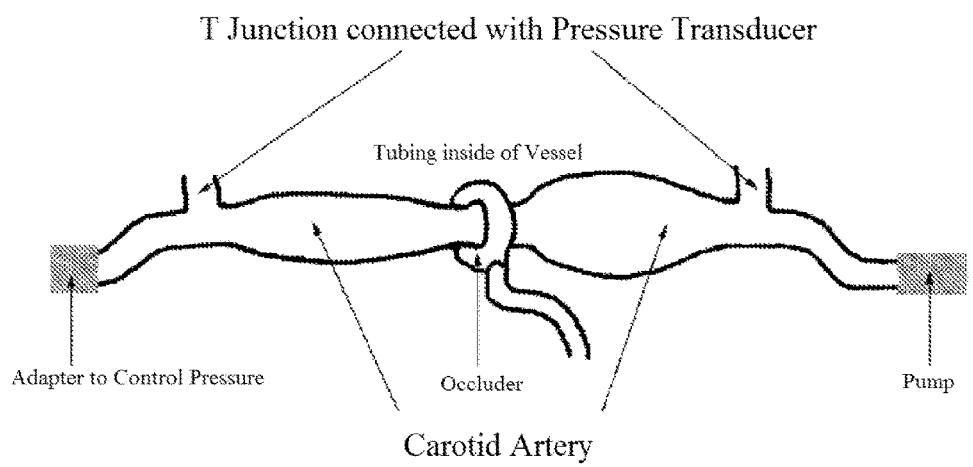

In another in vitro set-up, an arterial occluder was mounted around the carotid artery to create stenoses of different degrees (as shown in FIG. 7B). The occluder cuff has inner diameter and length of 4 and 5 mm, respectively, which can induce zero (no stenosis) to unity (full stenosis) area stenoses. The volumetric flow rate (Q) was measured by a perivascular flow probe (Transonic Systems Inc.; relative error of ±2% at full scale). The arteries were cannulated to T-junctions at both ends. The pressure transducers were connected to the T-junctions to measure the proximal and distal pressures ($P_{proximal}$ and $P_{distal}$, respectively) of the stenosis in order to determine the pressure gradient ($\Delta P = P_{proximal} - P_{distal}$). Pulsatile pressure and flow were continuously recorded using a Biopac MP 150 data acquisition system (Biopac Systems, Inc., Goleta, Calif.). A cast was made at 100 mmHg after the stenotic vessel was fixed with 6.25% glutaraldehyde solution in 0.1 sodium cacodylate buffer (osmolarity of fixative was 1,100 mosM). Photographs of small rings sectioned from the vessel and stenosis casts were then taken. The CSA measurements were made using the NIS-Elements imaging software for the cast (see the measured data in Table 1).

For the in vivo experiments, the analytical model was validated in coronary arteries. A sheath was introduced through the femoral artery to access the right coronary artery (RCA), left anterior descending artery (LAD artery), and left circumflex artery (LCx artery). After a midline sternotomy, the main trunk of these arteries was dissected free from the surrounding tissue in preparation for the placement of a flow probe and an inflatable occluder with no apparent major branches in between them. The coronary artery was gradually occluded by an inflatable occluder cuff to create different degrees of stenoses. The hyperemic volumetric flow rate (intracoronary injection of adenosine: 60 µg for left coronary artery and 30 µg for right coronary artery) was determined by a flow probe (Transonic Systems Inc.; relative error of ±2% at full scale). The distal pressure to coronary stenosis ($P_{distal}$) was measured by a Volcano ComboWire (Volcano Corp., San Diego, Calif.), which was inserted into the coronary artery through a sheath. The proximal, distal, and minimal CSAs were obtained from coronary angiograms using previous method (Kassab et al., Am. J. Physiol. Heart Circ. Physiol. 281: H623-628; Mollio et al., Circulation 104: 2351-2357).

2. Data Analysis

The proximal, distal, and minimal CSA and stenosis length, as well as hyperemic flow rate, were used to calculate the pressure drop (Equation 4), which was compared with the measurement obtained from in vitro and in vivo experiments. The relation of the pressure drop between analytical (or theoretical) model and experimental measurements was expressed as: $\Delta P_{experiment} = \alpha \cdot \Delta P_{theory} + \beta$. Myocardial FFR was calculated from the theoretical model (Equations [2] and [4]) in comparison with the in vivo coronary measurements. The empirical constants, $\alpha$ and $\beta$, were determined by a linear least-squares fit with corresponding correlation coefficients ($R^2$). In a Bland-Altman diagram, the difference of pressure drop and myocardial FFR between theoretical model and experimental measurements was plotted against their means. In the scatter diagram, the precision and bias of the analytical model were quantified. The root mean square (RMS) error was also determined to further assess the accuracy of the theoretical model.

3. Sensitivity Analysis

To determine the sensitivity of the model to various inputs (e.g., CSA and length of the lesion, hyperemic flow), parameters were varied over a range of values and determined the effect on pressure drop. The normalized pressure drop $$\left( \frac{\Delta P_{perturbed} - \Delta P_{actual}}{\Delta P_{actual}} \right)$$

was determined as a function of parameter $$X \left( \frac{X_{perturbed} - X_{actual}}{X_{actual}} \right)$$

which refers to distal CSA, stenosis CSA, stenosis length and flow rate in a vessel (actual or reference values of $$\frac{\pi \cdot 4.5^2}{4} \text{ mm}^2, \frac{\pi \cdot 1.7^2}{4} \text{ mm}^2,$$

10 mm and 111 ml/minute). The proximal CSA was not considered as it has a negligible effect on pressure drop. The actual pressure drop ($\Delta P_{actual}$) equaled to 9.4 mmHg when the dynamic viscosity of blood is 4.5 cp. The perturbed pressure drop ($\Delta P_{perturbed}$) was calculated by Equation [4] when $X_{actual}$ was changed to $X_{perturbed}$.

FIGS. 7A and B show in vitro stenosis set-up in carotid artery using concentric and eccentric tubings as well as an inflatable occluder cuff, whose geometry is shown in Table 1, The flow rates were varied in the range of 65-170 ml/min. If the entrance effect is omitted and the velocity profile is assumed to be uniform at the outlet of stenosis, the diffusive energy loss consists of only the viscous energy loss so that the pressure gradient in Equations [A11] or [A12] can be simplified to:

$$\Delta P_{theory} = \frac{\rho Q^2}{2} \left( \frac{1}{CSA_{outlet}^2} - \frac{1}{CSA_{inlet}^2} \right) + \int_0^{L_{vessel}} \frac{8\pi\mu}{CSA^2} Q dx + \frac{\rho Q^2}{2} \left( \frac{1}{CSA_{stenosis}} - \frac{1}{CSA_{distal}} \right)^2 \quad [5]$$

Equation [5] is the most straightforward model and can be found in standard textbook (see Miller, D. S., Internal Flow Systems: Design and Performance Prediction. (British Hydromechanics Research Association: 1990)). A least-squares fit showed a linear relation between $\Delta P_{theory}$ (Equation [5]) and in vitro $\Delta P_{experiment}$ as: $\Delta P_{experiment} = 1.98 \cdot \Delta P_{theory} - 0.72$ ($R^2 = 0.99$), which reflects poor agreement between theory and experiments. Equation [5] was also modified by multiplying the last term by an empirical coefficient of 1.52 as:

$$\Delta P_{theory} = \frac{\rho Q^2}{2} \left( \frac{1}{CSA_{outlet}^2} - \frac{1}{CSA_{inlet}^2} \right) + \quad [6]$$

-continued $$\int_0^{L_{vessel}} \frac{8\pi\mu}{CSA^2} Q dx + 1.52 \cdot \frac{\rho Q^2}{2}\left(\frac{1}{CSA_{stenosis}} - \frac{1}{CSA_{distal}}\right)^2$$

Figure 8A:
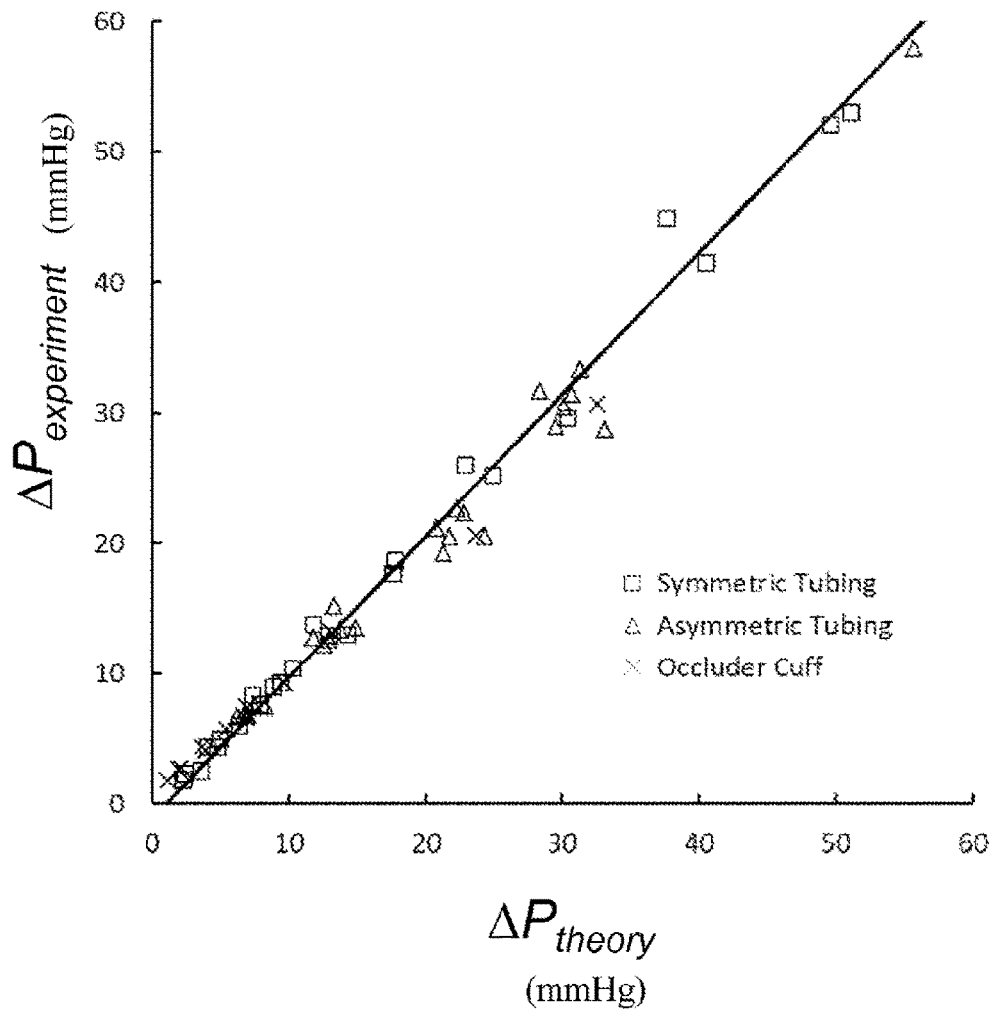
FIGS. 8A-B show (A) a graphical comparison of the pressure gradient between a model and in vitro carotid experiments and (B) a graphical plot of the pressure gradient between the model and in vitro experiments, according to embodiments of the present disclosure.
Figure 8B:
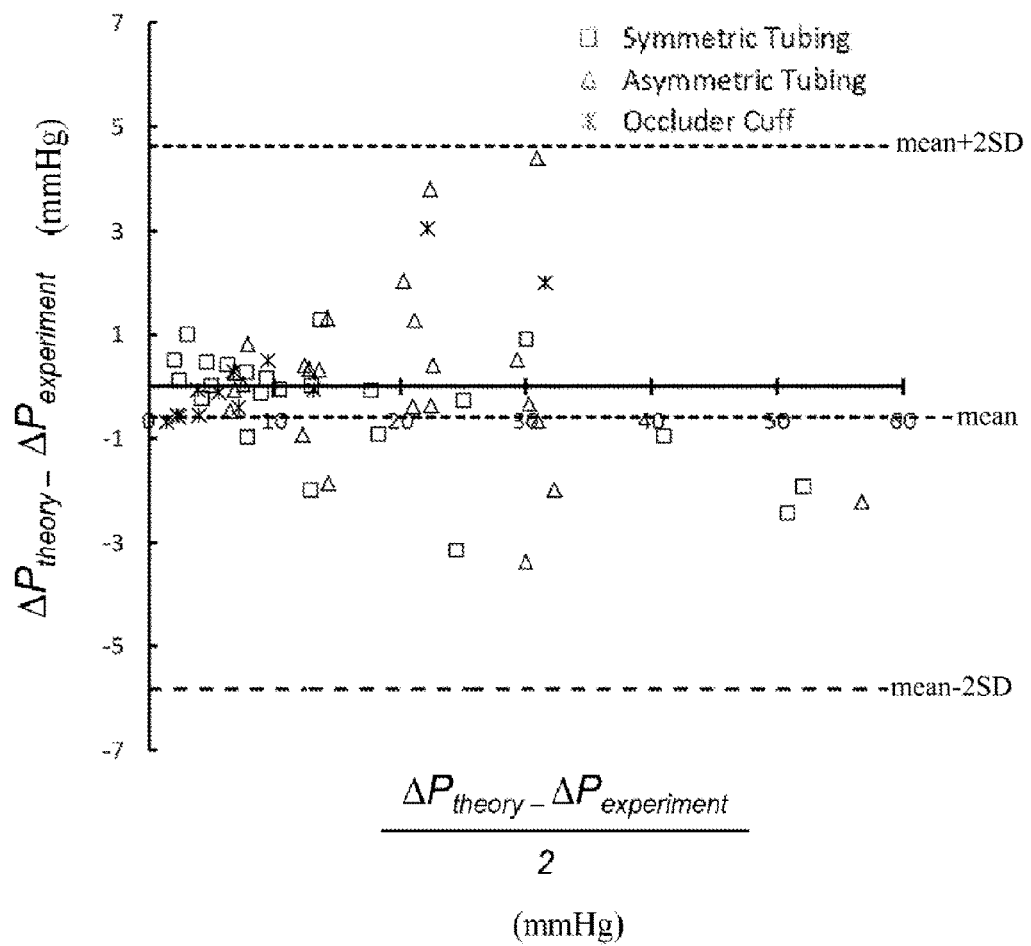

A least-squares fit showed a linear relation between $\Delta P_{theory}$ (Equation [5]) and in vitro $\Delta P_{experiment}$ as: $\Delta P_{experiment}=1.45\cdot\Delta P_{theory}-0.77$ ($R^2=0.98$). The in vitro experiments do not support the correction (i.e., Equation [6]), albeit it shows a slight improvement over Equation [5]. In contrast, FIG. 8A shows a comparison of pressure gradient between the present theoretical model (i.e., Equation [4] which can be expanded to Equations [A11] or [A12]) and in vitro experiments, which has a linear relation as: $\Delta P_{experiment}=1.08\cdot\Delta P_{theory}-1.15$ ($R^2=0.99$). It can be noted that no difference was observed for various stenotic segments (concentric, eccentric, cuff and various lengths). The experimental results were much more in agreement with the analytical model (Equation [4]) when both entrance effects at the inlet of stenosis and flow velocity profiles at the outlet of stenosis were considered and hence all subsequent calculations accounted for those factors. Moreover, the difference of –pressure gradients ($\Delta P_{theory}-\Delta P_{experiment}$) was plotted against the mean value $$\left(\frac{\Delta P_{theory}+\Delta P_{experiment}}{2}\right),$$

as shown in FIG. 8B. The mean systematic error (or bias) of the difference of pressure drops (−0.59 mmHg) was nearly zero, as expected because of the consistency of theoretical model and experimental measurements. Therefore, the 1 SD value (2.61 mmHg) was similar to the RMS error (2.66 mmHg) for the pressure difference. There was also very good correlation between $\Delta P_{theory}$ and $\Delta P_{experiment}$ experiment when the limits of agreement for Bland-Altman analysis were defined as the mean±2SD (4.6 and −5.8 mmHg), as shown in FIG. 8B. A comparison of in vitro pulsatile and steady-state flows shows a relative error of pressure drop<±5% so that the time-averaged flow rate (over a cardiac cycle) is used in Equation [4] for determination of pressure drop caused by coronary stenosis in the case of the relatively small Womersley and Reynolds numbers.

Figure 9A:
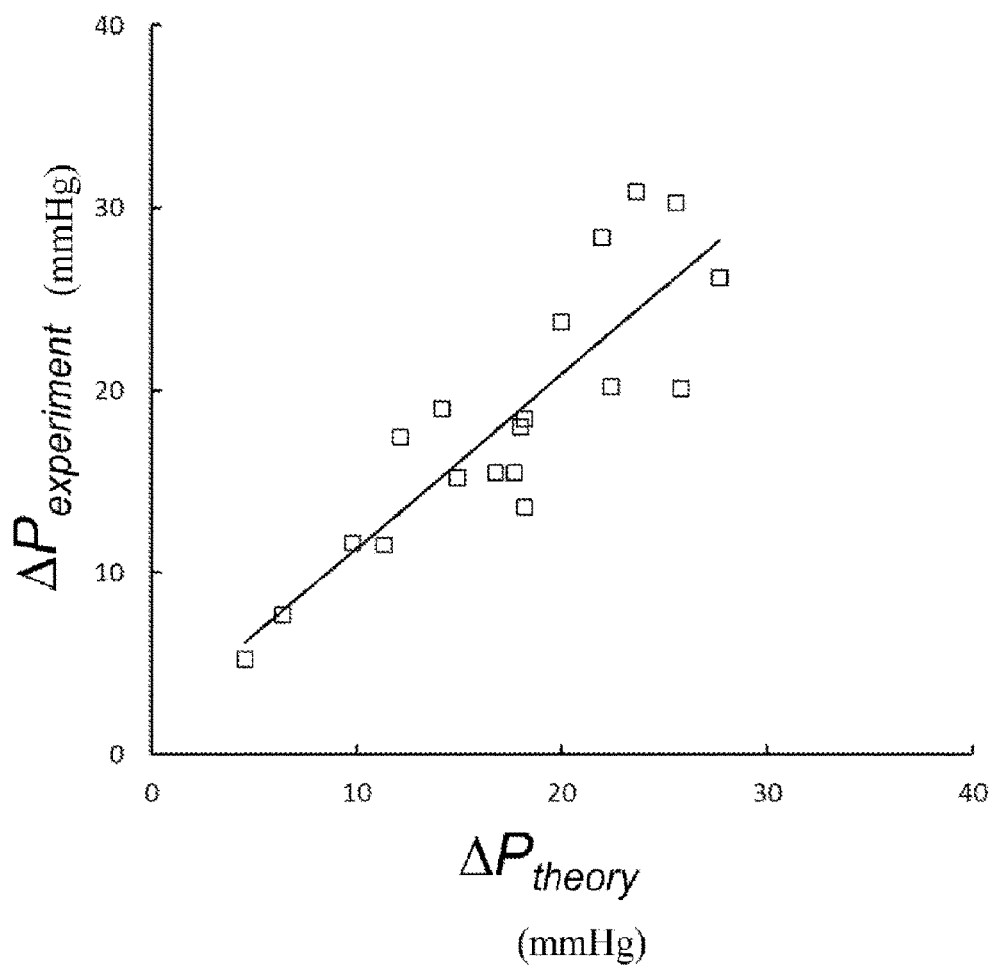
FIGS. 9A-B show (A) a graphical comparison of the pressure gradient between a model and in vitro carotid experiments and (B) a graphical plot of the pressure gradient between the model and in vitro experiments, according to embodiments of the present disclosure.
Figure 9B:
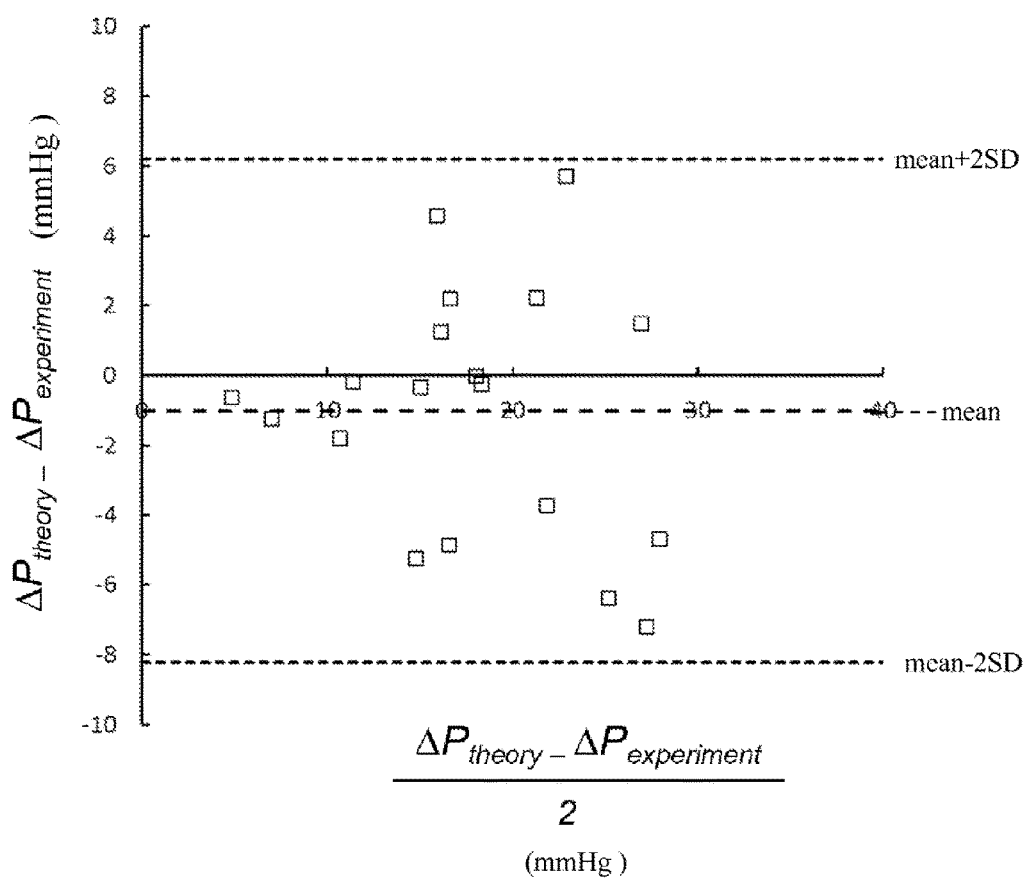

FIG. 9A shows a comparison of pressure drop between theoretical model (Equation [4]) and in vivo coronary experiments ($\Delta P_{theory}$ vs. $\Delta P_{experiment}$). A linear least-squares fit showed the relation as: $\Delta P_{experiment}=0.96\cdot\Delta P_{theory}+1.79$ ($R^2=0.75$). FIG. 9B shows a Bland-Altman plot for the pairwise comparisons of pressure drop between theoretical model and in vivo experiments, where the mean of pressure difference ($\Delta P_{theory}-\Delta P_{experiment}$) was −1.01, which was not significantly different from zero (P>>0.05). The RMS error of pressure difference between theoretical model and in vivo experiments was 3.65 mmHg.

Figure 10A:
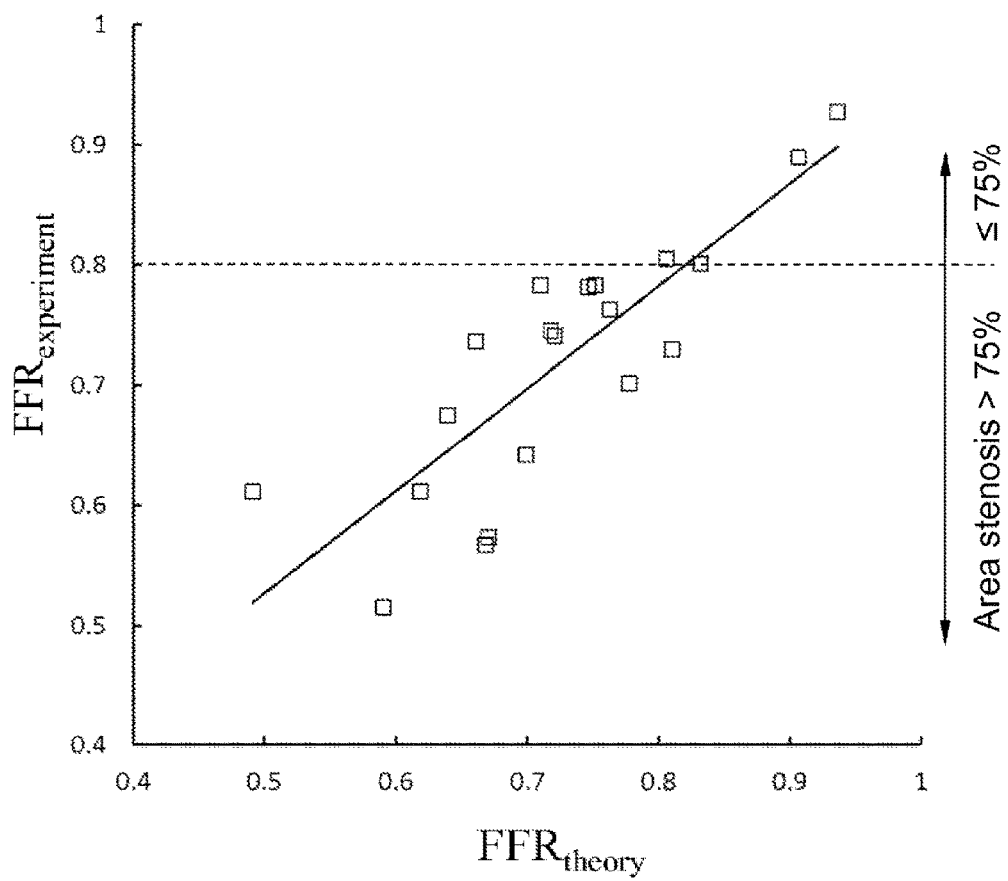
FIGS. 10A-B show (A) a graphical comparison of myocardial fractional flow reserve between a theoretical model and in vivo coronary experiments ($FFR_{theory}$ vs. $FFR_{experiment}$) and (B) a graphical plot of the pairwise comparison of myocardial FFR between the theoretical model and in vitro experiments, according to embodiments of the present disclosure.
Figure 10B:
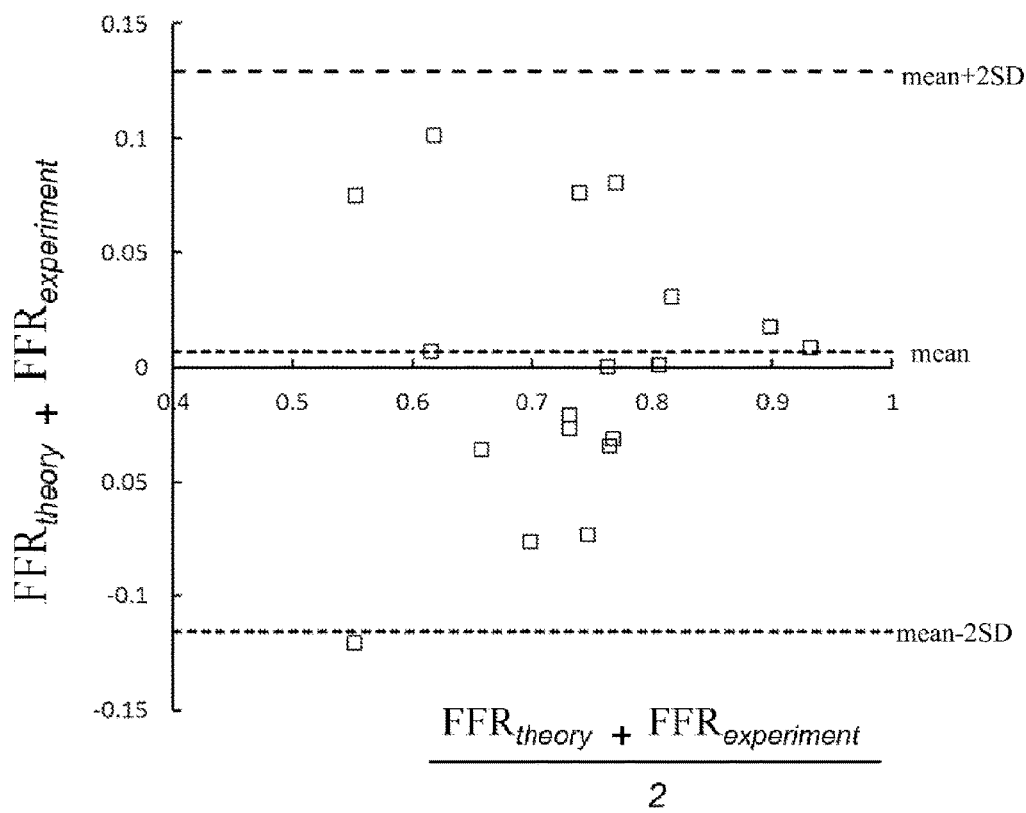

FIG. 10A shows the relationship of myocardial FFR between theoretical model (Equations [2] and [4]) and in vivo coronary experiments ($FFR_{theory}$ vs. $FFR_{experiment}$), expressed as: $FFR_{experiment}=0.85\cdot FFR_{theory}+0.1$ ($R^2=0.7$). Myocardial FFR was found to be less than 0.8 when the area stenosis was >75% (where $CSA_{proximal}$ is in the range of $\pi/4$ $3.8^2-\pi/4$ $4.5^2$ mm$^2$). Similar to the comparison of pressure drop in FIG. 9B, FIG. 10b shows a Bland-Altman plot for the pairwise comparisons of myocardial FFR between theoretical model and in vivo coronary experiments. There was good agreement of myocardial FFR between theoretical model and in vivo coronary experiments.

Figure 11:
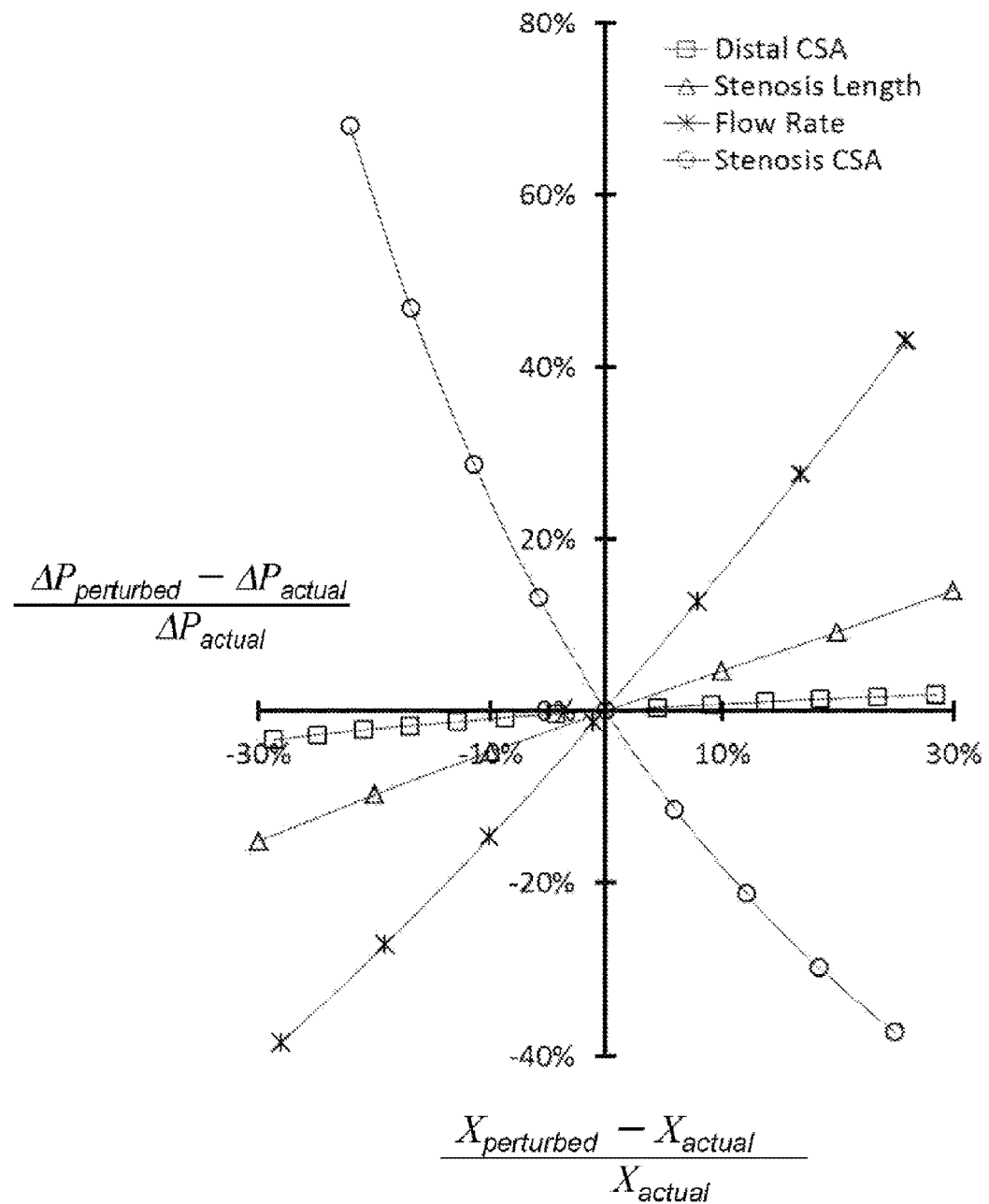
FIG. 11 shows a graphical representation of a sensitivity analysis for the distal cross-sectional area (CSA), stenosis CSA, stenosis length, and flow rate in a luminal organ, according to an embodiment of the present disclosure.

FIG. 11 shows a sensitivity analysis for the distal CSA, stenosis CSA, stenosis length and flow rate in a vessel. The pressure drop was strongly affected by stenosis CSA and flow rate whereas proximal CSA (not shown), distal CSA and stenosis length had relatively small effects.

What is claimed is:

1. A non-invasive method for determining fractional flow reserve within a luminal organ, the method comprising the steps of:

positioning a monitoring device external to a luminal organ at or near a stenosis, the monitoring device capable of determining at least one characteristic of the stenosis from such position, the monitoring device comprising an angiography device using angiography to determine the at least one characteristic of the stenosis;

operating the monitoring device to obtain a medical image of the luminal organ at or near the stenosis and non-invasively identify at least one characteristic of the stenosis directly from the medical image;

determining fractional flow reserve at or near the stenosis based upon at least the at least one characteristic identified by the monitoring device;

wherein the step of determining fractional flow reserve comprises the step of:

computing the fractional flow reserve using a data acquisition and processing system using an algorithm selected from the group consisting of the equation:

$$\Delta P = \frac{\rho Q^2}{2}\left(\frac{1}{CSA_{outlet}^2} - \frac{1}{CSA_{inlet}^2}\right) + \Delta P_{diffusive} + \Delta P_{expansion};$$

the equation:

$$FFR = \frac{P_{distal}}{P_a} = \frac{P_a - \Delta P}{P_a};$$

a combination thereof, and a mathematical equivalent of any of the aforementioned equations; and wherein $\Delta P$ is a pressure gradient along an axis of a segment of the luminal organ from a proximal position to a distal position of the stenosis, $\rho$ is a density of blood, Q is a hyperemic flow rate in the segment of the luminal organ determined based on an analytical model, $CSA_{outlet}$ is an outlet cross-sectional area, $CSA_{inlet}$ is an inlet cross-sectional area, $\Delta P_{diffusive}$ is a diffusive energy loss, and $\Delta P_{expansion}$ is an energy loss due to enlargement in cross-sectional area from the stenosis to a distal normal vessel segment, FFR is the fractional flow reserve, $P_a$ is a mean aortic pressure, and $P_{distal}$ is a hyperemic coronary pressure distal to the stenosis;

assessing hemodynamic function of the luminal organ based on the fractional flow reserve at or near the stenosis computed using the algorithm by comparing the computed fractional flow reserve to a comparison value in a database to determine the degree of stenosis; and treating the stenosis if the hemodynamic function assessed by computing the fractional flow reserve using the algorithm and comparing the fractional flow reserve to the comparison value in the database indicates the stenosis is functionally significant.

2. The method of claim 1, wherein the at least one characteristic is selected from the group consisting of a stenosis geometry and a flow rate in the vessel at or near the stenosis.

3. The method of claim 2, wherein the stenosis geometry comprises at least one geometry selected from the group consisting of a cross-sectional area of the luminal organ distal to the stenosis, a cross-sectional area of the luminal organ proximal to the stenosis, at least one cross-sectional area of the luminal organ at the stenosis, a percentage maximum stenosis of the luminal organ, and the length of the lesion of the luminal organ.

4. The method of claim 1, further comprising the step of:
diagnosing a disease based upon the determination of the fractional flow reserve within the vessel; and
wherein the step of determining fractional flow reserve at or near the stenosis is performed in less than about 2 minutes.

5. The method of claim 1, wherein the determination of fractional flow reserve is indicative of a degree of stenosis within the luminal organ.

6. The method of claim 1, wherein the step of determining fractional flow reserve is performed using a data acquisition and processing system in communication with the database containing one or more variables relating to the stenosis.

7. The method of claim 6, wherein the database contains a comparison value, and wherein the method further comprises the step of:
diagnosing a disease by comparing the determined fractional flow reserve to the comparison value.

8. The method of claim 1, wherein:
the monitoring device operates to noninvasively identify the at least one stenosis characteristic through angiography; and
the hyperemic flow rate is determined from a flow-diameter scaling law directly using an equation:

$$\text{Resistance} = \frac{99 \times 1333.22}{10 \times D_s^{7/3}} = \frac{13199}{10 \times D_s^{7/3}}$$

or the mathematical equivalent thereof, wherein $D_s$ is the diameter of the stenosis, and by mathematically calculating an impedance or admittance value within vessels of the luminal organ using the determined resistance value.

9. A non-invasive method for determining a flow rate within a luminal organ, the method comprising the steps of:
positioning a monitoring device external to a luminal organ at or near a stenosis, the monitoring device capable of determining at least one characteristic of the stenosis from such position, the monitoring device comprising an angiography device using angiography to determine the at least one characteristic of the stenosis;
operating the monitoring device to obtain a medical image of the luminal organ at or near the stenosis and noninsasively identify at least one characteristic of the stenosis directly from the medical image;
computing a flow rate at or near the stenosis based directly upon at least the at least one characteristic identified by the monitoring device;

wherein the step of computing the flow rate uses a data acquisition and processing system that uses the equation:

$$\Delta P = \frac{\rho Q^2}{2}\left(\frac{1}{CSA_{outlet}^2} - \frac{1}{CSA_{inlet}^2}\right) + \Delta P_{diffusive} + \Delta P_{expansion};$$

wherein $\Delta P$ is a pressure gradient along an axis of a segment of the luminal organ from a proximal position to a distal position of the stenosis, $\rho$ is a density of blood, Q is a hyperemic flow rate in the segment of the luminal organ, $CSA_{outlet}$ is an outlet cross-sectional area, $CSA_{inlet}$ is an inlet cross-sectional area, $\Delta P_{diffusive}$ is a diffusive energy loss, and $\Delta P_{expansion}$ is an energy loss due to enlargement in cross-sectional area from the stenosis to a distal normal vessel segment;
assessing hemodynamic function of the luminal organ based on the fractional flow reserve at or near the stenosis computed using the algorithm by comparing the computed fractional flow reserve to a comparison value in a database to determine the degree of stenosis; and
treating the stenosis if the hemodynamic function assessed by computing the fractional flow reserve using the algorithm and comparing the fractional flow reserve to the comparison value in the database indicates the stenosis is functionally significant.

10. The method of claim 9, wherein the at least one characteristic is a stenosis geometry at or near the stenosis and wherein the hyperemic flow rate is determined from a flow-diameter scaling law directly using an equation:

$$\text{Resistance} = \frac{99 \times 1333.22}{10 \times D_s^{7/3}} = \frac{13199}{10 \times D_s^{7/3}}$$

or the mathematical equivalent thereof, wherein $D_s$ is the diameter of the stenosis.

11. The method of claim 9, wherein the method further comprises the step of:
determining fractional flow reserve at or near the stenosis using a data acquisition and processing system and the equation:

$$FFR = \frac{P_{distal}}{P_a} = \frac{P_a - \Delta P}{P_a}$$

or a mathematical equivalent thereof, wherein FFR is the fractional flow reserve, $P_a$ is a mean aortic pressure, and $P_{distal}$ is a hyperemic coronary pressure distal to the stenosis.

12. The method of claim 11, wherein the data acquisition and processing system is in communication with a database containing a comparison value, and wherein the method further comprises the step of:
diagnosing a disease by comparing the determined fractional flow reserve to the comparison value; and
wherein the step of computing the flow rate at or near the stenosis is performed in less than about 2 minutes.

13. A system for non-invasively determining fractional flow reserve of a fluid within a luminal organ, the system comprising:
a monitoring device for determining fractional flow reserve, the monitoring device configured to obtain a medical image of a luminal organ at or near a stenosis and detect, directly from the medical image, at least one stenosis characteristic of the luminal organ when the device is positioned externally of the luminal organ, the monitoring device comprising an angiography device using angiography to determine the at least one characteristic of the stenosis; and a data acquisition and processing system in communication with the monitoring device, the data acquisition and processing system configured to calculate a fractional flow reserve directly from at least the at least one stenosis characteristic;

wherein the data acquisition and processing system is configured to calculate the fractional flow reserve using the equation:

$$FFR = \frac{P_{distal}}{P_a} = \frac{P_a - \Delta P}{P_a}$$

or a mathematical equivalent thereof, wherein FFR is the fractional flow reserve, $P_a$ is a mean aortic pressure, $P_{distal}$ is a hyperemic coronary pressure distal to the stenosis, and $\Delta P$ is a pressure gradient along an axis of a segment of the luminal organ from a proximal position to a distal position of the stenosis, to assess hemodynamic function of the luminal organ based on the fractional flow reserve at or near the stenosis computed using the algorithm by comparing the computed fractional flow reserve to a comparison value in a database to determine the degree of stenosis, and to treat the stenosis if the hemodynamic function assessed by computing the fractional flow reserve using the algorithm and comparing the fractional flow reserve to the comparison value in the database indicates the stenosis is functionally significant.

14. The system of claim 13, wherein the at least one stenosis characteristic is selected from the group consisting of a stenosis geometry and a flow rate in the luminal organ at or near the stenosis and wherein the hyperemic flow rate is determined directly using a flow-diameter scaling law comprising an equation:

$$\text{Resistance} = \frac{99 \times 1333.22}{10 \times D_s^{7/3}} = \frac{13199}{10 \times D_s^{7/3}}$$

or the mathematical equivalent thereof, wherein $D_s$ is the diameter of the stenosis.

15. The system of claim 13, wherein the stenosis characteristic comprises at least one geometry selected from the group consisting of a cross-sectional area of the luminal organ distal to the stenosis, a cross-sectional area of the luminal organ proximal to the stenosis, at least one cross-sectional area of the luminal organ at the stenosis, a percentage maximum stenosis of the luminal organ, and the length of the lesion of the luminal organ.

16. The system of claim 13, wherein the system is capable of diagnosing a disease based upon the calculation of the fractional flow reserve within the vessel and wherein the system is capable of calculating fractional flow reserve in less than about 2 minutes.

17. The system of claim 13, wherein the calculation of fractional flow reserve is indicative of a degree of stenosis within the luminal organ.

18. The system of claim 13, wherein the data acquisition and processing system is further operable to calculate the flow rate at or near the stenosis based directly upon at least the at least one characteristic directly determined by the monitoring device, without the use of a numerical model, and using the equation:

$$\Delta P = \frac{\rho Q^2}{2} \left( \frac{1}{CSA_{outlet}^2} - \frac{1}{CSA_{inlet}^2} \right) + \Delta P_{diffusive} + \Delta P_{expansion}$$

or a mathematical equivalent thereof, wherein $\rho$ is a density of blood, Q is a hyperemic flow rate in the segment of the luminal organ, $CSA_{outlet}$ is an outlet cross-sectional area, $CSAi_{nlet}$ is an inlet cross-sectional area, $\Delta P_{diffusive}$ is a diffusive energy loss, and $\Delta P_{expansion}$ is an energy loss due to enlargement in cross-sectional area from the stenosis to a distal normal vessel segment.

19. The system of claim 13, wherein the monitoring device operates to directly detect the at least one stenosis characteristic through angiography.

20. The system of claim 13, wherein the data acquisition and processing system is in communication with a database containing a comparison value, and wherein the data acquisition and processing system is operable to diagnose a disease by comparing the determined fractional flow reserve to the comparison value.

* * * * *